(12) United States Patent
Park et al.

(10) Patent No.: US 9,099,653 B2
(45) Date of Patent: Aug. 4, 2015

(54) ELECTROACTIVE MATERIALS

(75) Inventors: Kyung-Ho Park, Wilmington, DE (US);
Nora Sabina Radu, Landenberg, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 1141 days.

(21) Appl. No.: 12/628,491

(22) Filed: Dec. 1, 2009

(65) Prior Publication Data

US 2010/0187506 A1 Jul. 29, 2010

Related U.S. Application Data

(60) Provisional application No. 61/118,717, filed on Dec. 1, 2008.

(51) Int. Cl.
| | |
|---|---|
| *H01L 51/54* | (2006.01) |
| *C07C 211/54* | (2006.01) |
| *H01L 51/00* | (2006.01) |
| *C07C 211/58* | (2006.01) |
| *C09K 11/06* | (2006.01) |
| *H01L 51/50* | (2006.01) |

(52) U.S. Cl.
CPC .......... *H01L 51/0035* (2013.01); *C07C 211/54* (2013.01); *C07C 211/58* (2013.01); *C09K 11/06* (2013.01); *C09K 2211/1007* (2013.01); *C09K 2211/1011* (2013.01); *C09K 2211/1014* (2013.01); *H01L 51/5012* (2013.01); *H01L 51/5048* (2013.01)

(58) Field of Classification Search
None
See application file for complete search history.

(56) References Cited

U.S. PATENT DOCUMENTS

| | | |
|---|---|---|
| 5,707,747 A | 1/1998 | Tomiyama et al. |
| 5,929,194 A | 7/1999 | Woo et al. |
| 5,962,631 A | 10/1999 | Woo et al. |
| 6,259,202 B1 | 7/2001 | Sturm et al. |
| 6,303,238 B1 | 10/2001 | Thompson et al. |
| 6,670,645 B2 | 12/2003 | Grushin et al. |
| 6,872,475 B2 | 3/2005 | Chen et al. |
| 6,953,705 B2 | 10/2005 | Prakash |
| 7,023,013 B2 | 4/2006 | Ricks et al. |
| 7,189,989 B2 | 3/2007 | Ise |
| 7,235,420 B2 | 6/2007 | Prakash et al. |
| 7,540,978 B2 | 6/2009 | Pfeiffer et al. |
| 7,745,017 B2 | 6/2010 | Nakamura et al. |
| 7,887,933 B2 | 2/2011 | Kathirgamanathan et al. |
| 8,063,399 B2 * | 11/2011 | Johansson et al. ............... 257/40 |
| 8,343,381 B1 | 1/2013 | Chesterfield |
| 2001/0026878 A1 | 10/2001 | Woo et al. |
| 2002/0048687 A1 | 4/2002 | Hosokawa et al. |
| 2002/0155319 A1 | 10/2002 | Kawamura et al. |
| 2003/0168970 A1 | 9/2003 | Tominaga et al. |
| 2003/0224205 A1 | 12/2003 | Li et al. |
| 2004/0004433 A1 | 1/2004 | Lamansky et al. |
| 2004/0038459 A1 | 2/2004 | Brown et al. |
| 2004/0082250 A1 | 4/2004 | Haoto |
| 2004/0102577 A1 | 5/2004 | Hsu et al. |
| 2004/0127637 A1 | 7/2004 | Hsu et al. |
| 2004/0263067 A1 | 12/2004 | Saitoh et al. |
| 2005/0073249 A1 | 4/2005 | Morii et al. |
| 2005/0184287 A1 | 8/2005 | Herron |
| 2005/0186106 A1 | 8/2005 | Li et al. |
| 2005/0191776 A1 | 9/2005 | Lamansky et al. |
| 2005/0205860 A1 | 9/2005 | Hsu et al. |
| 2006/0033421 A1 | 2/2006 | Matsuura et al. |
| 2006/0216411 A1 | 9/2006 | Steudel et al. |
| 2007/0031588 A1 | 2/2007 | Nakayama |
| 2007/0032632 A1 | 2/2007 | Tsukioka et al. |
| 2007/0079927 A1 | 4/2007 | Lamansky et al. |
| 2007/0096082 A1 | 5/2007 | Gaynor et al. |
| 2007/0126345 A1* | 6/2007 | Hudack et al. ................. 313/504 |
| 2007/0181874 A1 | 8/2007 | Prakash et al. |
| 2007/0228364 A1 | 10/2007 | Radu et al. |
| 2007/0285009 A1 | 12/2007 | Kubota |
| 2008/0071049 A1 | 3/2008 | Radu et al. |
| 2008/0097076 A1 | 4/2008 | Radu et al. |
| 2008/0102312 A1 | 5/2008 | Parham et al. |
| 2008/0138655 A1 | 6/2008 | Lecloux et al. |
| 2008/0303427 A1 | 12/2008 | Johansson et al. |
| 2009/0051281 A1 | 2/2009 | Inoue et al. |
| 2009/0184635 A1 | 7/2009 | Pan et al. |
| 2009/0206748 A1 | 8/2009 | Moriwaki et al. |
| 2010/0108989 A1 | 5/2010 | Büsing et al. |
| 2010/0187507 A1 | 7/2010 | Park et al. |
| 2010/0213825 A1 | 8/2010 | Park et al. |
| 2011/0095269 A1 | 4/2011 | Zhang et al. |

FOREIGN PATENT DOCUMENTS

| | | |
|---|---|---|
| EP | 681019 A2 | 9/1999 |
| EP | 1277824 A1 | 1/2003 |
| EP | 1624500 A1 | 2/2006 |
| EP | 1933603 A1 | 6/2008 |
| JP | 08167479 A | 6/1996 |
| JP | 11224779 A | 8/1999 |
| JP | 11338172 A | 12/1999 |
| JP | 2000068073 A | 3/2000 |
| JP | 2000186066 A | 7/2000 |
| JP | 2001039933 A | 2/2001 |
| JP | 2001226331 A | 8/2001 |
| JP | 2003/026641 A | 1/2003 |
| JP | 2003238501 A | 8/2003 |
| JP | 2004014187 A | 1/2004 |
| JP | 2004/107292 A | 4/2004 |
| JP | 2006/328037 A | 12/2006 |
| JP | 2007182432 A | 7/2007 |
| KR | 1020050073233 A | 7/2005 |
| KR | 100702763 B1 | 4/2007 |
| KR | 1020070091293 A | 9/2007 |
| KR | 100765728 B1 | 10/2007 |
| WO | 9954385 A1 | 10/1999 |
| WO | 0053565 A1 | 9/2000 |
| WO | 0070655 A2 | 11/2000 |
| WO | 0141512 A1 | 6/2001 |
| WO | 02051958 A1 | 7/2002 |
| WO | 03/008424 A1 | 1/2003 |
| WO | 03/040257 A1 | 5/2003 |
| WO | 03/063555 A1 | 7/2003 |
| WO | 03/091688 A2 | 11/2003 |
| WO | 2004/016710 A1 | 2/2004 |
| WO | 2004041901 A1 | 5/2004 |
| WO | 2005/052027 A1 | 6/2005 |
| WO | 2005049546 A1 | 6/2005 |
| WO | 2005049548 A1 | 6/2005 |
| WO | 2005049689 A2 | 6/2005 |
| WO | 2006063852 A1 | 6/2006 |
| WO | 2007065678 A1 | 6/2007 |
| WO | 2007076146 A2 | 7/2007 |
| WO | 2008011953 A1 | 1/2008 |
| WO | 2009067419 A1 | 5/2009 |
| WO | 2010065494 A2 | 6/2010 |

OTHER PUBLICATIONS

Machine English translation of Nishiyama et al. (JP 2004-107292 A). Mar. 3, 2013.*
CRC Handbook of Chemistry and Physics, 81$^{st}$ Edition (2000-2001) (Book Not Included).
Kirk-Othmer Concise Encyclopedia of Chemical Technology, 4th Edition, p. 1537 & pp. 837-860 (1999) (Book Not Included).
"Flexible light-emitting diodes made from soluble conducting polymer," Nature vol. 357, pp. 477 479 (Jun. 11, 1992).
International Search report, Korean Intellectual Property Office, Daejeon, KR, PCT/US2009/066188, PCT Counterpart of the present application, Hyun Shik Oh, Authorized Officer, May 27, 2010.
Kirk-Othmer Encyclopedia of Chemical Technology, Fourth Edition, vol. 18, p. 837-860, 1996, by Y. Wang.
Borello et al., "Photodetectors," Kirk-Othmer Encyclopedia of Chemical Technology, Fourth Edition, 1999, vol. 18, pp. 1537-1538.
Colon et al., "High Molecular Weight Aromatic Polymers by Nickel Coupling of Aryl Polychlorides," Journal of Polymer Science, Part A, Polymer Chemistry Edition, 1990, vol. 28, 367.
Eaton et al., "Dihedral Angle of Biphenyl in Solution and the Molecular Force Field," Journal of the Chemical Society, Faraday Transactions 2, 1973, 60, pp. 1601-1608.
He et al, "A Hole-Transporting Material with Controllabel Morphology Containing Binaphthyl and Triphenylamine Chromophores," Advanced Functional Materials, vol. 16, No. 10, 2006, pp. 1343-1348.
Lee et al., "A Thermally Stable Hole Injection Material for Use in Organic Light-Emitting Diodes," Thin Solid Films, 2007, vol. 515, pp. 7726-7731.
Markus—Photoconductive Cell, Electronics and Nucleonics Dictionary, 1966, pp. 470, 471 and 476 McGraw-Hill.

Noji et al., "A New Catalytic System for Aerobic Oxidative Coupling of 2-Naphthol Derivatives by the Use of CuCl-Amine Complex: A Practical Synthesis of Binaphthol Derivatives," Tetrahedron Letters, 1994, vol. 35, No. 43, pp. 7983-7984.
Yamamoto et al, Electrically conducting and thermally stable-conjugated poly(arylene)s prepared by organometallic process, Progress in Polymer Science, 1992, vol. 17, pp. 1153-1205.
Zhao et al., "Solid-State Dye-Sensitized Photovoltaic Device with Newly Designed Small Organic Molecule as Hole-Conductor," Chemical Physical Letters, 2007, vol. 445, pp. 259-264.
Extended European Search Report for Application No. 09830950.3; EPO; Jun. 1, 2012.
Extended European Search Report for Application No. 09831094.9 counterpart to U.S. Appl. No. 12/630,361; EPO; Jun. 13, 2012.
Extended European Search Report for Application No. 12166882.6; Jul. 18, 2012.
Extended European Search Report for Application No. 09830952.9, counterpart to U.S. Appl. No. 12/628,503; Oct. 2, 2012.
Extended European Search Report for Application No. 09830951.1, counterpart to U.S. Appl. No. 12/628,491; Oct. 9, 2012.
First Official Action; EPO; Application No. 08756397.9, counterpart to U.S. Appl. No. 12/129,785; Oct. 27, 2011.
PCT International Search Report for Application No. PCT/US2008/065016, counterpart to U.S. Appl. No. 12/129,785; M. Redecker Authorized Officer; EPO; Oct. 12, 2008.
PCT International Search Report for Application No. PCT/US2008/065191, counterpart to U.S. Appl. No. 12/129,729; W. Fitz, Authorized Officer; Sep. 4, 2008.
PCT International Search Report for Application No. PCT/US2008/083844, counterpart to U.S. Appl. No. 12/272,210; S. Saldamli, Authorized Officer; Jan. 28, 2009.
PCT International Search Report for Application No. PCT/US2009/066184; Kim Ju Seung, Authorized Officer; KIPO; Jul. 6, 2010.
PCT International Search Report for Application No. PCT/US2009/066194, counterpart to U.S. Appl. No. 12/628,503; Oh Hyun Shik, Authorized Officer; KIPO; Jul. 7, 2010.
PCT International Search Report for Application No. PCT/US2009/066513, counterpart to U.S. Appl. No. 12/630,361; Oh Hyun Shik, Authorized Officer; KIPO; Jul. 7, 2010.
Chen et al., "Efficient, Blue Light-Emitting Dliodes Using Cross-Linked Layers of Polymeric Arylamine and Fluorene," Synthetic Metals, 1999, vol. 107, pp. 129-135.
Zhu et al., "Effect of ITO Carrier Concentration on the Performance of Light-Emitting Diodes," 2000; Material Research Society; Chem Abstract 134: 122994.
He et al., "High-Efficiency Organic Polymer Light-Emitting Heterostructure Devices on Flexible Plastic Substrates," Applied Physics Letters, 2000, vol. 76, No. 6, pp. 661-663.

* cited by examiner

*Primary Examiner* — J. L. Yang

(57) ABSTRACT

There is provided a compound having Formula I or Formula II:

Formula I

-continued

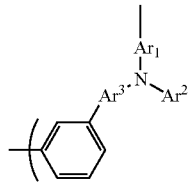

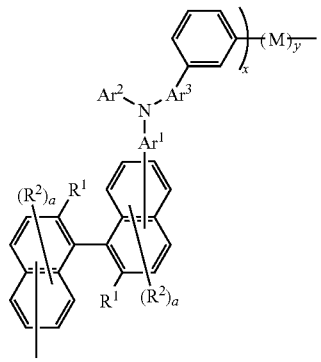

-continued

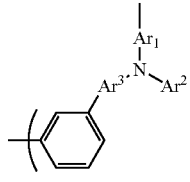

Formula II

In the Formula: $Ar^1$ is a single bond or an arylene; $Ar^2$ is an aryl group; $Ar^3$ is a single bond or an arylene; $R^1$ is selected from H, D, aryl groups, alkyl groups, silyl groups, siloxane groups, fluoroalkyl groups, alkoxy groups, and fluoroalkoxy groups, or the two $R^1$ groups may be joined together to form an aliphatic ring having 5-10 carbons; $R^2$ is selected from D, aryl groups, alkyl groups, silyl groups, siloxane groups, fluoroalkyl groups, alkoxy groups, or fluoroalkoxy groups; M is a conjugated moiety; a is an integer from 0 to 2; b is an integer from 0 to 3; n is an integer equal to or greater than 1; and x and y are mole fractions where x+y=1.0.

22 Claims, 1 Drawing Sheet

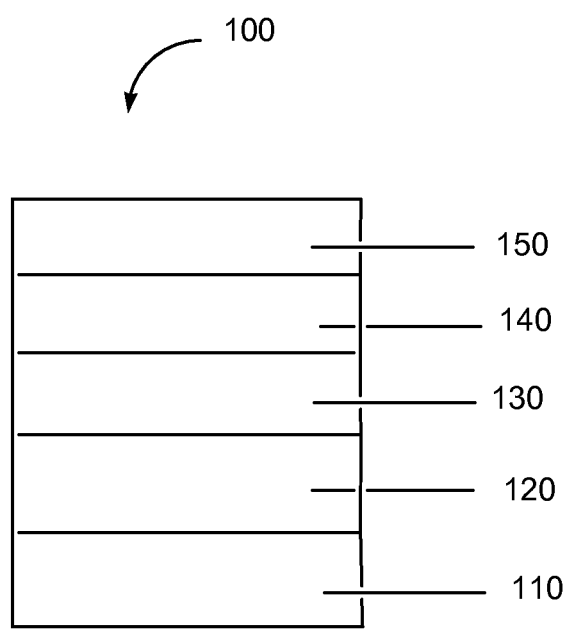

ELECTROACTIVE MATERIALS

RELATED APPLICATION

This application claims priority under 35 U.S.C. §119(e) from U.S. Provisional Application No. 61/118,717 filed Dec. 1, 2008 which is incorporated by reference in its entirety.

BACKGROUND INFORMATION

1. Field of the Disclosure

The present invention relates to novel electroactive compounds. The invention further relates to electronic devices having at least one active layer comprising such an electroactive compound.

2. Description of the Related Art

In organic photoactive electronic devices, such as organic light emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used. Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

There is a continuing need for charge transport materials for use in electronic devices.

SUMMARY

There is provided a compound having Formula I or Formula II:

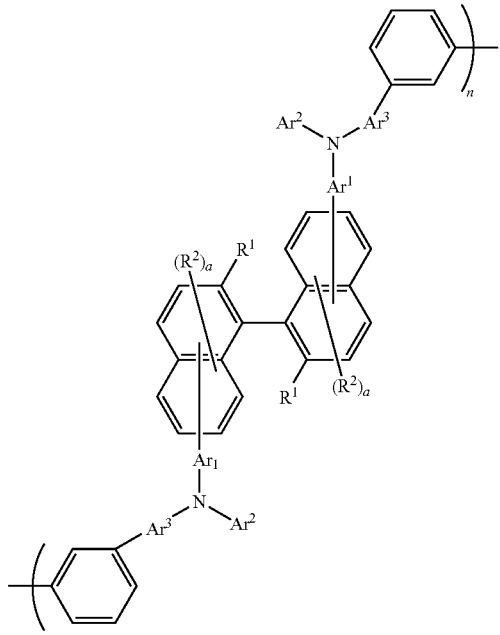

Formula I

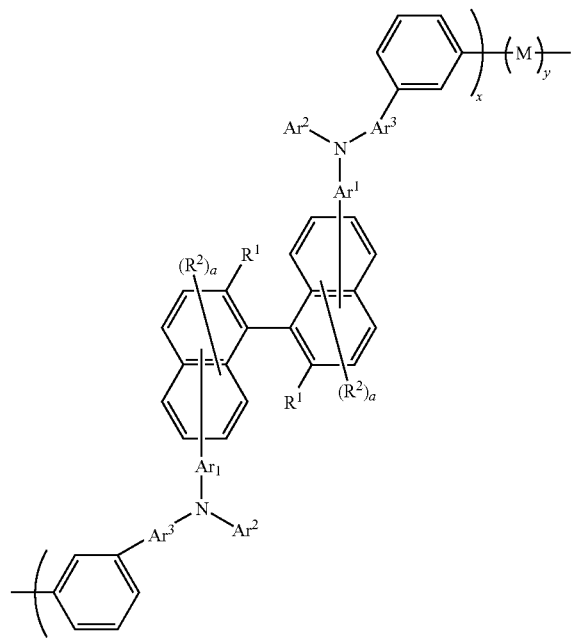

Formula II wherein:
Ar$^1$ is the same or different at each occurrence and is selected from the group consisting of a single bond and an arylene;
Ar$^2$ is the same or different at each occurrence and is an aryl group;
Ar$^3$ is the same or different at each occurrence and is selected from the group consisting of a single bond and an arylene;
R$^1$ is the same or different at each occurrence and is selected from the group consisting of H, D, aryl groups, alkyl groups, silyl groups, siloxane groups, fluoroalkyl groups, alkoxy groups, and fluoroalkoxy groups, or the two R$^1$ groups may be joined together to form an aliphatic ring having 5-10 carbons;
R$^2$ is the same or different at each occurrence and is selected from the group consisting of D, aryl groups, alkyl groups, silyl groups, siloxane groups, fluoroalkyl groups, alkoxy groups, and fluoroalkoxy groups;
M is the same or different at each occurrence and is a conjugated moiety;
a is the same or different at each occurrence and is an integer from 0 to 5;
n is an integer equal to or greater than 2; and
x and y are mole fractions such that x+y=1.0, with the proviso that x and y are not zero.

There is also provided an electronic device having at least one layer comprising above compound having Formula I or Formula II.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided a compound having Formula I or Formula II:

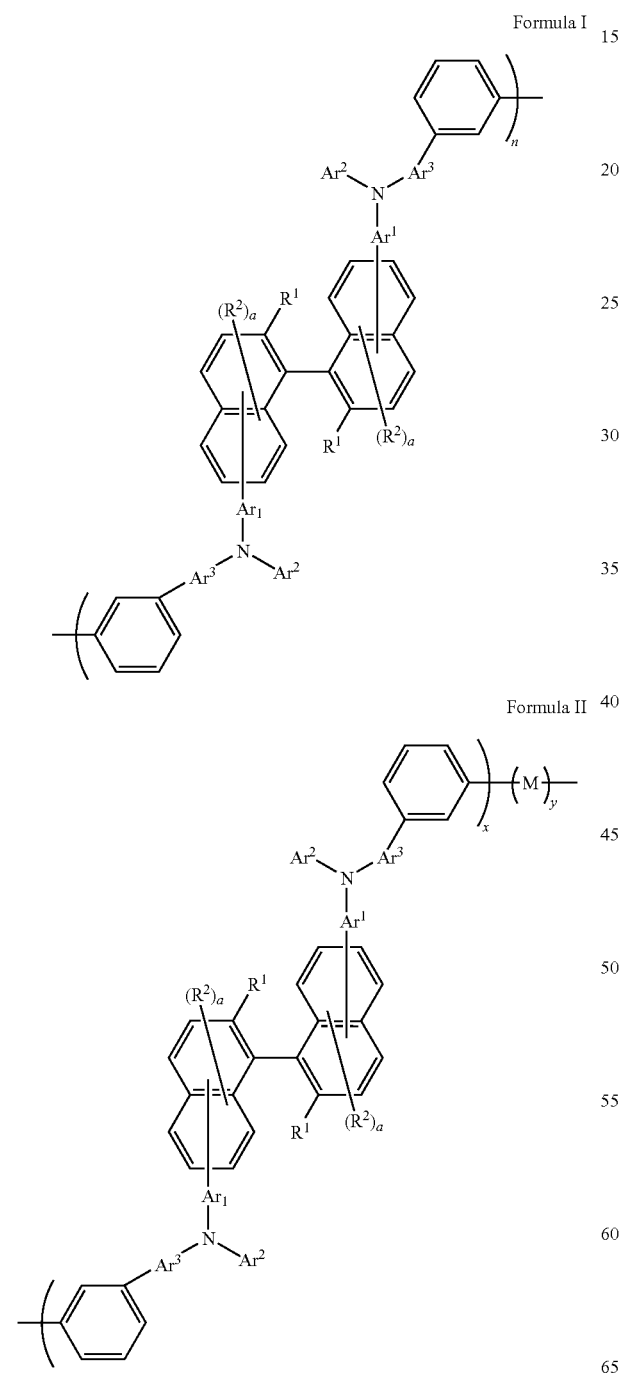

wherein:
Ar¹ is the same or different at each occurrence and is selected from the group consisting of a single bond and an arylene;
Ar² is the same or different at each occurrence and is an aryl group;
Ar³ is the same or different at each occurrence and is selected from the group consisting of a single bond and an arylene;
R¹ is the same or different at each occurrence and is selected from the group consisting of H, D, aryl groups, alkyl groups, silyl groups, siloxane groups, fluoroalkyl groups, alkoxy groups, and fluoroalkoxy groups, or the two R¹ groups may be joined together to form an aliphatic ring having 5-10 carbons;
R² is the same or different at each occurrence and is selected from the group consisting of D, aryl groups, alkyl groups, silyl groups, siloxane groups, fluoroalkyl groups, alkoxy groups, and fluoroalkoxy groups;
M is the same or different at each occurrence and is a conjugated moiety;
a is the same or different at each occurrence an integer from 0 to 5;
n is an integer equal to or greater than 2; and
x and y are mole fractions such that x+y=1.0, with the proviso that x and y are not zero.

There is also provided an electronic device having at least one layer comprising a compound having Formula I or Formula II.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Electroactive Compound, the Electronic Device, and finally Examples.

1. Definitions and Clarification of Terms

Before addressing details of embodiments described below, some terms are defined or clarified.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tertbutyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aryl" means an aromatic carbocyclic moiety, which may be a single ring (monocyclic) or multiple rings (bicyclic, or more) fused together or linked covalently. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments, aryl groups have 6 to 60 carbon atoms; in some embodiments 6 to 48 carbon atoms. The term is intended to include heteroaryl groups. Heteroaryl groups may have from 4-50 carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include alkyl, aryl, nitro, cyano, —N($R^7$)($R^8$), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxane, thioalkoxy, —S(O)$_2$—N(R')(R"), —C(=O)—N(R')(R"), (R')(R")N-alkyl, (R')(R")N-alkoxyalkyl, (R')(R")N -alkylaryloxyalkyl, —S(O)$_s$-aryl (where s=0-2) or —S(O)$_s$-heteroaryl (where s=0-2). Each R' and R" is independently an optionally substituted alkyl, cycloalkyl, or aryl group. R' and R", together with the nitrogen atom to which they are bound, can form a ring system in certain embodiments. Substituents may also be crosslinking groups.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport material facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "crosslinkable group" or "crosslinking group" is intended to mean a group than can lead to crosslinking via thermal treatment or exposure to radiation. In some embodiments, the radiation is UV or visible.

The term "electroactive" as it refers to a layer or a material, is intended to indicate a layer or material which electronically facilitates the operation of the device. Examples of active materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The prefix "fluoro" is intended to indicate that one or more hydrogens in a group has been replaced with fluorine.

The prefix "hetero" indicates that one or more carbon atoms has been replaced with a different atom. In some embodiments, the heteroatom is O, N, S, or combinations thereof.

The term "oxyalkyl" is intended to mean a heteroalkyl group having one or more carbons replaced with oxygens. The term includes groups which are linked via an oxygen.

The term "photoactive" is intended to mean to any material that exhibits electroluminescence or photosensitivity.

The term "silyl" refers to the group $R_3Si$—, where R is H, D, C1-20 alkyl, fluoroalkyl, or aryl. In some embodiments, one or more carbons in an R alkyl group are replaced with Si. In some embodiments, the silyl groups are (hexyl)$_2$Si(Me)CH$_2$CH$_2$Si(Me)$_2$- and [CF$_3$(CF$_2$)$_6$CH$_2$CH$_2$]$_2$SiMe-.

The term "siloxane" refers to the group $(RO)_3Si$—, where R is H, D, C1-20 alkyl, or fluoroalkyl.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics, 81$^{st}$ Edition* (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Electroactive Compound

The compound described herein has Formula I or Formula II:

Formula I

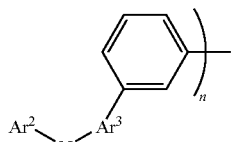
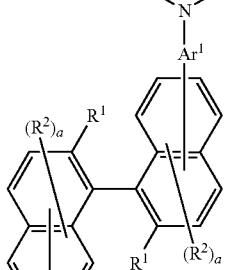
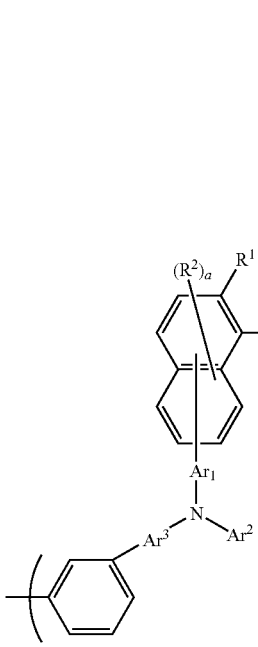

Formula II wherein:

Ar¹ is the same or different at each occurrence and is selected from the group consisting of a single bond and an arylene;

Ar² is the same or different at each occurrence and is an aryl group;

Ar³ is the same or different at each occurrence and is selected from the group consisting of a single bond and an arylene;

$R^1$ is the same or different at each occurrence and is selected from the group consisting of H, D, aryl groups, alkyl groups, silyl groups, siloxane groups, fluoroalkyl groups, alkoxy groups, and fluoroalkoxy groups, or the two $R^1$ groups may be joined together to form an aliphatic ring having 5-10 carbons;

$R^2$ is the same or different at each occurrence and is selected from the group consisting of D, aryl groups, alkyl groups, silyl groups, siloxane groups, fluoroalkyl groups, alkoxy groups, and fluoroalkoxy groups;

M is the same or different at each occurrence and is a conjugated moiety;

a is the same or different at each occurrence an integer from 0 to 5;

n is an integer equal to or greater than 2; and x and y are mole fractions such that x+y=1.0, with the proviso that x and y are not zero.

In the formulae, a bond drawn through the center of a fused ring system indicates that the substituent can be bonded to any available carbon in the fused ring.

The compounds of Formula I and Formula II have a 1,1'-binaphthyl core which has aryl amino groups further linked through a meta linkage. The compounds have good hole transport properties. When these materials are used in the hole transport layer of OLEDs, the resulting devices can have good efficiency and lifetime. In some embodiments, the compounds can be used as hosts for light-emitting materials in light-emitting layers of devices.

In some embodiments, the compound has Formula Ia with a 3,3'-binaphthyl linkage.

Formula Ia

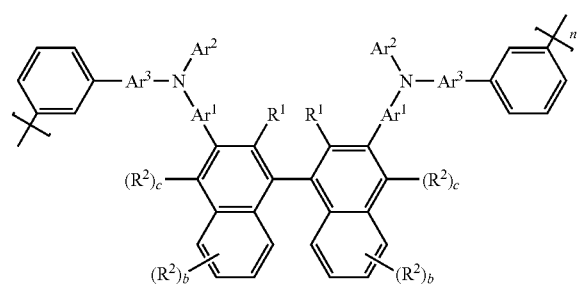

In some embodiments, the compound has Formula Ib with a 4,4'-binaphthyl linkage.

Formula Ib

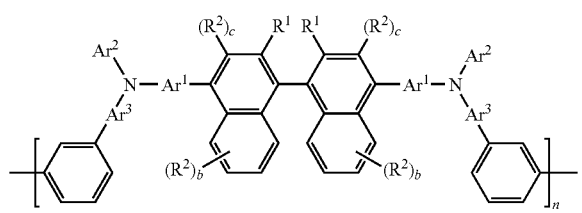

In some embodiments, the compound has Formula Ic with a 5,5'-binaphthyl linkage.

Formula Ic

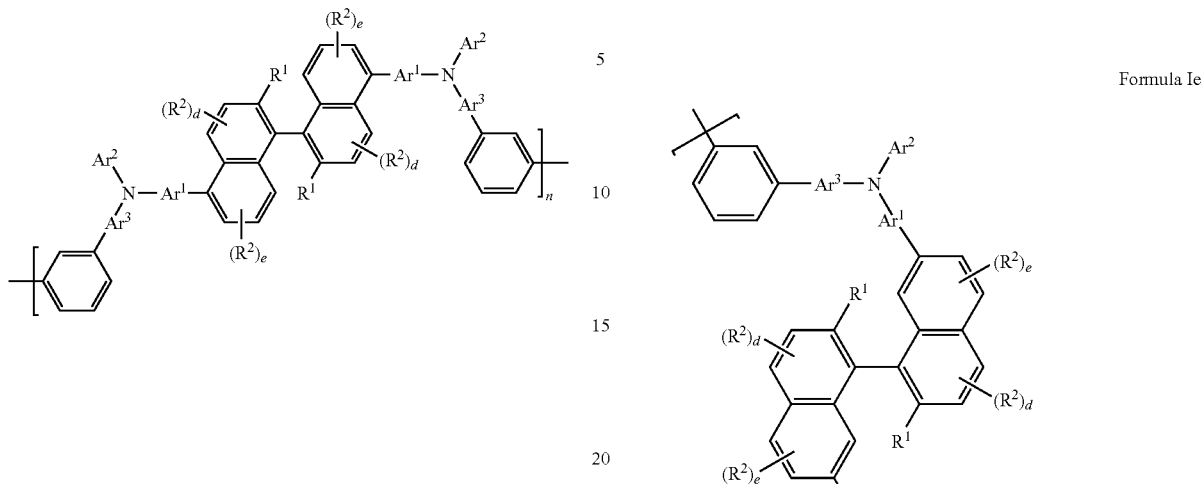

In some embodiments, the compound has Formula Id with a 6,6'-binaphthyl linkage.

Formula Id

In some embodiments, the compound has Formula Ie with a 7,7'-binaphthyl linkage.

Formula Ie

In Formulae Ia-e:
Ar$^1$, Ar$^2$, Ar$^3$, R$^1$, R$^2$ and n are as defined above;
b is the same or different at each occurrence and is an integer from 0 to 4;
c is the same or different at each occurrence and is an integer from 0 to 1;
d is the same or different at each occurrence and is an integer from 0 to 2; and
e is the same or different at each occurrence and is an integer from 0 to 3.

In some embodiments, the compound is selected from the group consisting of Formula IIa having a 3,3'-binaphthyl linkage; Formula IIb having a 4,4'-binaphthyl linkage; Formula IIc having a 5,5'-binaphthyl linkage; Formula IId having a 6,6'-binaphthyl linkage; and Formula IIe having a 7,7'-binaphthyl linkage.

Formula IIa

-continued

Formula IIb

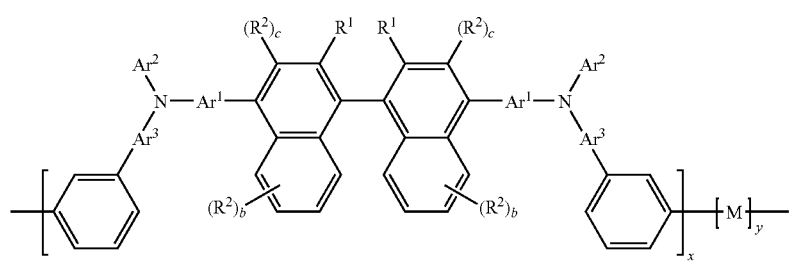

Formula IIc

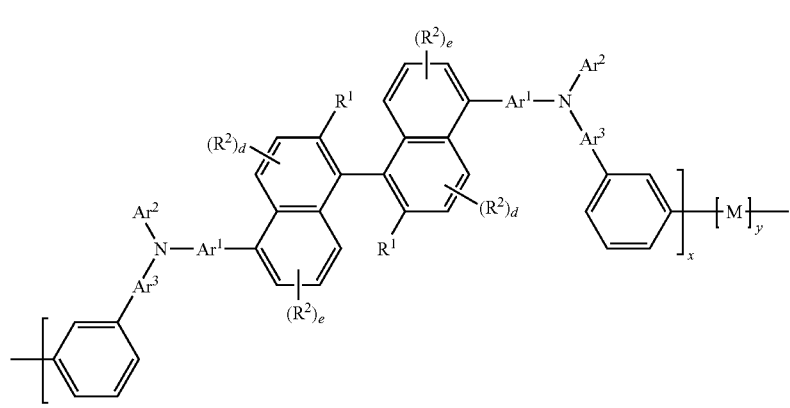

Formula IId

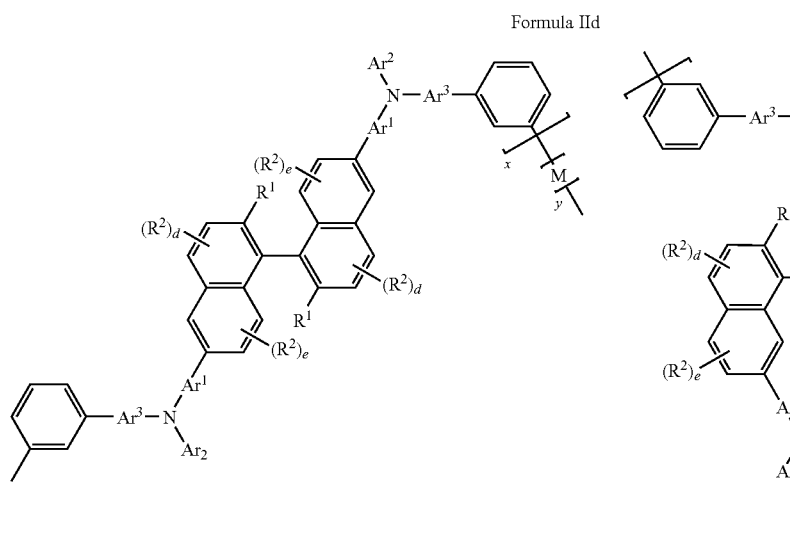

Formula IIe

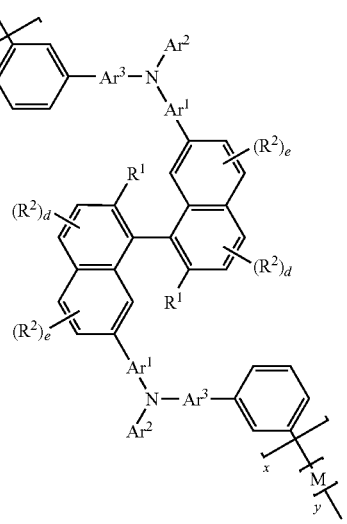

In Formulae IIa-e:
Ar$^1$, Ar$^2$, Ar$^3$, R$^1$, R$^2$, and M are as defined above;
b is the same or different at each occurrence and is an integer from 0 to 4;
c is the same or different at each occurrence and is an integer from 0 to 1;
d is the same or different at each occurrence and is an integer from 0 to 2; and
e is the same or different at each occurrence and is an integer from 0 to 3.

In some embodiments, Ar$^1$ has Formula III

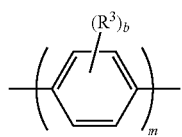

Formula III where:
R³ is the same or different at each occurrence and is selected from the group consisting of D, alkyl, alkoxy, siloxane and silyl;
b is the same or different at each occurrence and is an integer from 0-4; and
m is the same or different at each occurrence and is an integer from 1 to 6.

In some embodiments, at least one of one b is not zero. In some embodiments, m=1–3.

In some embodiments, Ar¹ is selected from the group consisting of a single bond, phenylene, p-biphenylene, p-terphenylene, naphthylene, phenylenenaphthylene, and naphthylenephenylene. In some embodiments, Ar¹ is selected from the group consisting of phenylene and biphenylene.

In some embodiments, Ar² has Formula IV

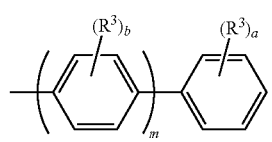

Formula IV where:
R³ is the same or different at each occurrence and is selected from the group consisting of alkyl, alkoxy, siloxane and silyl;
a is an integer from 0 to 5;
b is the same or different at each occurrence and is an integer from 0 to 4; and
m is the same or different at each occurrence and is an integer from 1 to 6.

In some embodiments of Formula IV, at least one of one a and b is not zero. In some embodiments, m=1–3. In some embodiments, Ar² is selected from the group consisting phenyl, biphenyl, terphenyl, and naphthyl.

In some embodiments, Ar³ has Formula III, as defined above. In some embodiments of Formula III, at least one b is not zero. In some embodiments, m=1–3. In some embodiments, Ar³ is selected from the group consisting of a single bond, phenylene, biphenylene, and naphthylene. In some embodiments, Ar³ is selected from the group consisting of phenylene and biphenylene.

Any of Ar¹, Ar² and Ar³, when not a single bond, may be substituted at any position. The substituents may be present to improve one or more physical properties of the compound, such as solubility. In some embodiments, the substituents are selected from the group consisting of D, alkyl groups, silyl groups, siloxane groups, and alkoxy groups. In some embodiments, the groups have from 1-12 carbon atoms. In some embodiments, adjacent alkyl groups are joined together to form a non-aromatic ring. In some embodiments, there is at least one substituent which includes a crosslinkable group. In some embodiments, crosslinking substituents are present on at least one Ar². Examples of crosslinkable groups include, but are not limited to vinyl, acrylate, perfluorovinylether, 1-benzo-3,4-cyclobutane, siloxane, cyanate groups, cyclic ethers (epoxides), cycloalkenes, and acetylenic groups. In one embodiment, the crosslinkable group is vinyl.

In some embodiments, R¹ is selected from an alkyl group having 1-12 carbon atoms and an alkoxy group having 1-12 carbon atoms.

In some embodiments, R² is selected an alkyl group having 1-12 carbon atoms and an alkoxy group having 1-12 carbon atoms.

In some embodiments, a and b are selected from 0 and 1. In some embodiments, a=b=0.

In some embodiments, n=1 and the compound is not polymeric. In some embodiments, n is 2 or greater and the compound is an oligomer or polymer. In some embodiments, n is greater than 20.

Formula II represents a copolymer in which there is at least one other conjugated moiety. In some embodiments, x is at least 0.4. In some embodiments, x is in the range of 0.4 to 0.6. The copolymers can be random, alternating, or block copolymers. In some embodiments, M is an aromatic unit having triarylamine units. In some embodiments, M is an aromatic group. In some embodiments, M is an aromatic unit having a crosslinkable substituent. The amount of M having a crosslinkable substituent is generally between 4 and 20 mole percent.

When R¹ is not H or D, the substituted binaphthyl group introduces non-planarity into the backbone of the compound having Formula I or Formula II. The first naphthyl group is oriented in a plane that is different from the second naphthyl group to which it is linked. Because of the non-planarity, the compounds are chiral. In general, they are formed as racemic mixtures. Some non-limiting examples of compounds having Formula I include Compounds A-D below.

Compound A
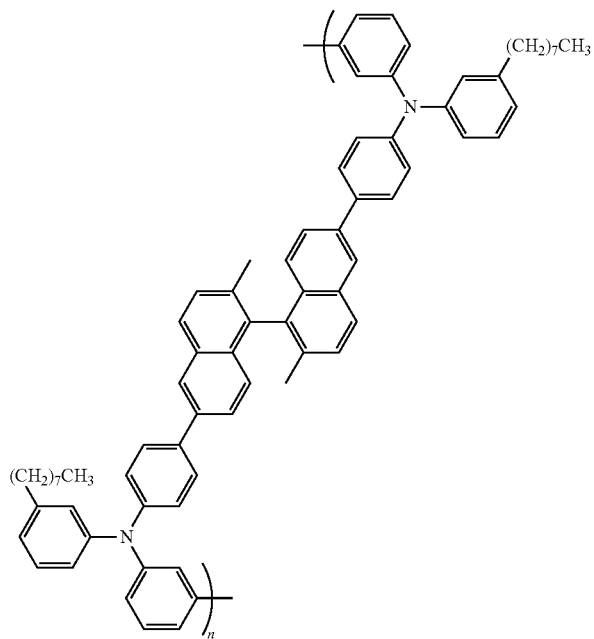
Compound B
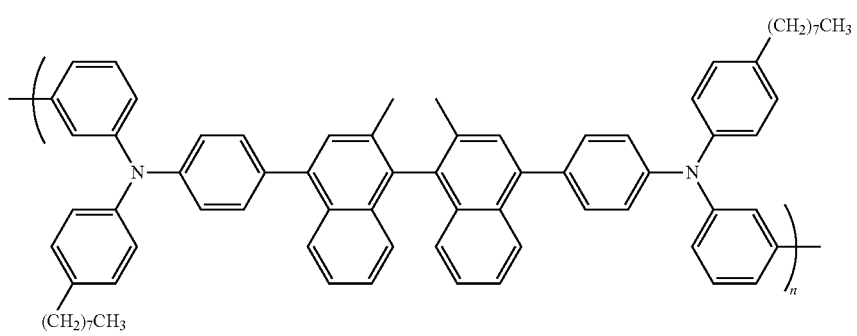
Compound C
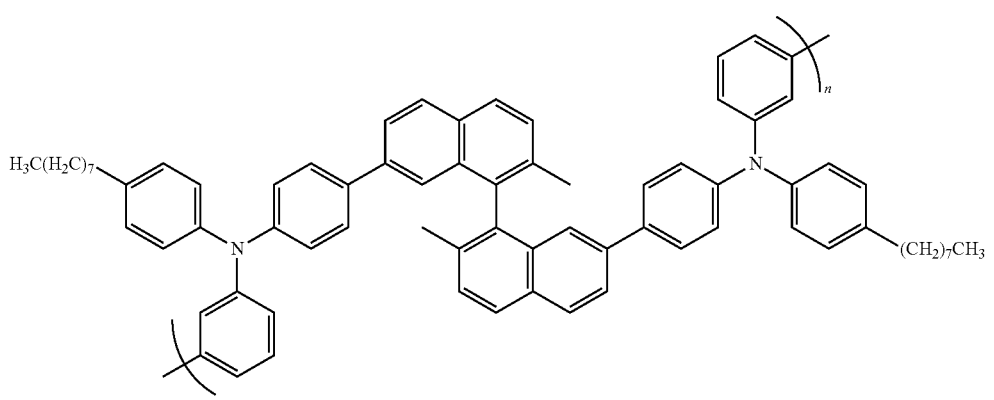

-continued

Compound D

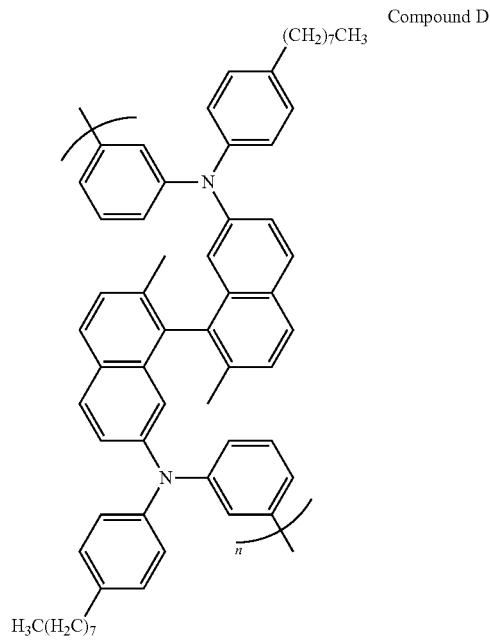

The new compounds can be made using any technique that will yield a C—C or C—N bond. A variety of such techniques are known, such as Suzuki, Yamamoto, Stille, and other transition metal catalyzed coupling reactions. The compounds can be formed into layers using solution processing techniques. The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing. When crosslinking groups are present, the films can be heated and/or treated with UV light to form crosslinked films. The crosslinked films are more robust to additional processing steps and generally are not soluble in processing solvents.

The new compounds described herein have can be used as hole transport materials, as photoactive materials, and as hosts for photoactive materials. The new compounds have hole mobilities and HOMO/LUMO energies similar to efficient small molecule hole transport compounds such as N,N'-diphenyl-N,N'-bis(3-methylphenyl)-[1,1'-biphenyl]-4,4'-diamine (TPD) and N,N'-bis(naphthalen-1-yl)-N,N'-bis-(phenyl)benzidine (α-NPB). Compounds such as TPD and NPD generally must be applied using a vapor deposition technique.

In some embodiments, the new compounds are useful as hosts for photoactive materials.

3. Electronic Devices

Organic electronic devices that may benefit from having one or more layers comprising at least one compound as described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure is shown in FIG. 1. The device 100 has an anode layer 110 and a cathode layer 150, and a photoactive layer 130 between them. Adjacent to the anode is a layer 120 comprising a charge transport material, for example, a hole transport material. Adjacent to the cathode may be a charge transport layer 140 comprising an electron transport material. As an option, devices may use one or more additional hole injection or hole transport layers (not shown) next to the anode 110 and/or one or more additional electron injection or electron transport layers (not shown) next to the cathode 150.

As used herein, the term "photoactive" refers to a material that emits light when activated by an applied voltage (such as in a light-emitting diode or light-emitting electrochemical cell), or responds to radiant energy and generates a signal with or without an applied bias voltage (such as in a photodetector). In one embodiment, a photoactive layer is an emitter layer.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Kirk-Othmer Concise Encyclopedia of Chemical Technology, 4$^{th}$ edition, p. 1537, (1999).

In some embodiments, the hole transport layer 120 comprises at least one new electroactive compound as described herein.

In some embodiments, the photoactive layer 130 comprises at least one new electroactive compound as described herein, wherein the electroactive compound is photoactive.

In some embodiments, the photoactive layer 130 comprises at least one new electroactive compound as described herein, wherein the electroactive compound serves as a host having a photoactive material dispersed therein.

The other layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8 10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

In some embodiments, the device further comprises a buffer layer between the anode and the layer comprising the new polymer. The term "buffer layer" is intended to mean a layer comprising electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Buffer materials may be polymers, oligomers, or small molecules, and may be in the form of solutions, dispersions, suspensions, emulsions, colloidal mixtures, or other compositions. The buffer layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The buffer layer can comprise charge transfer compounds, and the like, such as copper phthalocyanine and the tetrathiafulvalene-tetracyanoquinodimethane system (TTF-TCNQ). In one embodiment, the buffer layer is made from a dispersion of a conducting polymer and a colloid-forming polymeric acid. Such materials have been described in, for example, published U.S. patent applications 2004-0102577, 2004-0127637, and 2005/205860.

In some embodiments, hole transport layer 120 comprises the new electroactive compound described herein. In some embodiments, layer 120 comprises other hole transport materials. Examples of other hole transport materials for layer 120 have been summarized for example, in Kirk Othmer Encyclopedia of Chemical Technology, Fourth Edition, Vol. 18, p. 837 860, 1996, by Y. Wang. Both hole transporting molecules and polymers can be used. Commonly used hole transporting molecules include, but are not limited to: N,N'-diphenyl-N, N'-bis(3-methylphenyl) -[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis (3-methylphenyl)-N,N,N',N'-2,5-phenylenediamine (PDA), a-phenyl 4-N,N -diphenylaminostyrene (TPS), p-(diethylamino)benzaldehyde diphenylhydrazone (DEH), triphenylamine (TPA), bis[4 (N,N-diethylamino) -2-methylphenyl](4-methylphenyl)methane (MPMP), 1-phenyl-3-[p -(diethylamino)styryl]-5-[p-(diethylamino)phenyl]pyrazoline (PPR or DEASP), 1,2-trans-bis(9H-carbazol-9-yl)cyclobutane (DCZB), N,N,N',N' tetrakis(4-methylphenyl)-(1,1'-biphenyl)-4,4'-diamine (TTB), N,N'-Bis(naphthalen-1-yl)-N, N'-bis-(phenyl)benzidine (α-NPB), and porphyrinic compounds, such as copper phthalocyanine. Commonly used hole transporting polymers include, but are not limited to, polyvinylcarbazole, (phenylmethyl)polysilane, and polyaniline. It is also possible to obtain hole transporting polymers by doping hole transporting molecules such as those mentioned above into polymers such as polystyrene and polycarbonate. Buffer layers and/or hole transport layer can also comprise polymers of thiophene, aniline, or pyrrole with polymeric fluorinated sulfonic acids, as described in published US applications 2004/102577, 2004/127637, and 2005/205860.

Any organic electroluminescent ("EL") material can be used as the photoactive material in layer 130, including, but not limited to, small molecule organic fluorescent compounds, fluorescent and phosphorescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. In some cases the small molecule fluorescent or organometallic materials are deposited as a dopant with a host material to improve processing and/or electronic properties. Examples of conjugated polymers include, but are not limited to poly(phenylenevinylenes), polyfluorenes, poly (spirobifluorenes), polythiophenes, poly(p-phenylenes), copolymers thereof, and mixtures thereof. The materials may also be present in admixture with a host material. In some embodiments, the host material is a hole transport material or an electron transport material. In some embodiments, the host is the new electroactive compound described herein. In some embodiments, the ratio of host material to photoactive material is in the range of 5:1 to 20:1; in some embodiments, 10:1 to 15:1.

Examples of electron transport materials which can be used in the electron transport layer 140 and/or the optional layer between layer 140 and the cathode include metal chelated oxinoid compounds, such as tris(8-hydroxyquinolato) aluminum (AlQ), bis(2-methyl-8-quinolinolato)(p -phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1, 2,4-triazole (TAZ), and 1,3,5-tri(phenyl-2-benzimidazole)

benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

The choice of materials for each of the component layers is preferably determined by balancing the goals of providing a device with high device efficiency with device operational lifetime. Other layers may also be present in the device. There may be one or more hole injection and/or hole transport layers between the buffer layer and the organic active layer. There may be one or more electron transport layers and/or electron injection layers between the organic active layer and the cathode.

The device can be prepared by a variety of techniques, including sequentially depositing the individual layers on a suitable substrate. Substrates such as glass and polymeric films can be used. Conventional vapor deposition techniques can be used, such as thermal evaporation, chemical vapor deposition, and the like. Alternatively, the organic layers can be applied by liquid deposition using suitable solvents. The liquid can be in the form of solutions, dispersions, or emulsions. Typical liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing, any conventional coating or printing technique, including but not limited to spin-coating, dip-coating, roll-to-roll techniques, ink jet printing, screen-printing, gravure printing and the like.

The new electroactive compounds described herein can be applied by liquid deposition from a liquid composition. The term "liquid composition" is intended to mean a liquid medium in which a material is dissolved to form a solution, a liquid medium in which a material is dispersed to form a dispersion, or a liquid medium in which a material is suspended to form a suspension or an emulsion. Any liquid medium in which the compound is dissolved or dispersed and from which it will form a film can be used. In one embodiment, the liquid medium consists essentially of one or more organic solvents. In one embodiment the organic solvent is an aromatic solvent. In one embodiment, the organic liquid is selected from chloroform, dichloromethane, toluene, anisole, and mixtures thereof. The new compound can be present in the liquid medium in a concentration of 0.2 to 2 percent by weight. Other weight percentages of the new compound may be used depending upon the liquid medium.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layer 140, 50-2000 Å, in one embodiment 100-1000 Å; cathode 150, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In one embodiment, the device has the following structure, in order: anode, buffer layer, hole transport layer, photoactive layer, electron transport layer, electron injection layer, cathode. In one embodiment, the anode is made of indium tin oxide or indium zinc oxide. In one embodiment, the buffer layer comprises a conducting polymer selected from the group consisting of polythiophenes, polyanilines, polypyrroles, copolymers thereof, and mixtures thereof. In one embodiment, the buffer layer comprises a complex of a conducting polymer and a colloid-forming polymeric acid.

In one embodiment, the hole transport layer comprises the new compound described herein. In one embodiment, the hole transport layer consists essentially of the new electroactive compound described herein.

In one embodiment, the photoactive layer comprises the new electroactive compound described herein and a photoactive compound. In one embodiment, the photoactive layer further comprises a second host material. In some embodiments, the photoactive layer consists essentially of the new electroactive compound described herein and a photoactive compound. In some embodiments, the photoactive material is present in an amount of at least 1% by weight. In some embodiments, the photoactive material is 2-20% by weight.

In one embodiment, the electron transport layer comprises a metal complex of a hydroxyaryl-N-heterocycle. In one embodiment, the hydroxyaryl-N-heterocycle is unsubstituted or substituted 8-hydroxyquinoline.

In one embodiment, the electron injection layer is LiF or $Li_2O$. In one embodiment, the cathode is Al or Ba/Al.

In one embodiment, the device is fabricated by liquid deposition of the buffer layer, the hole transport layer, and the photoactive layer, and by vapor deposition of the electron transport layer, the electron injection layer, and the cathode.

Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Example 1

This example illustrates the preparation of a monomer which can be used to form an electroactive compound, Compound C.

(a) The starting material ditriflate 1 was synthesized from the scheme described below.

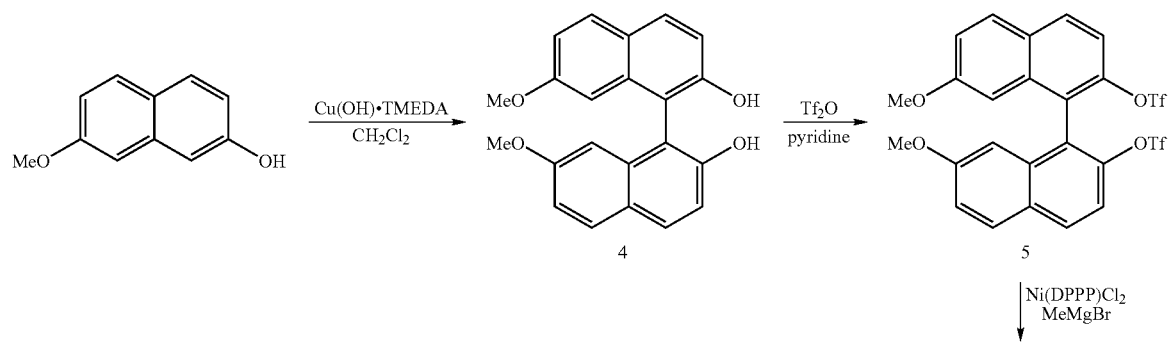
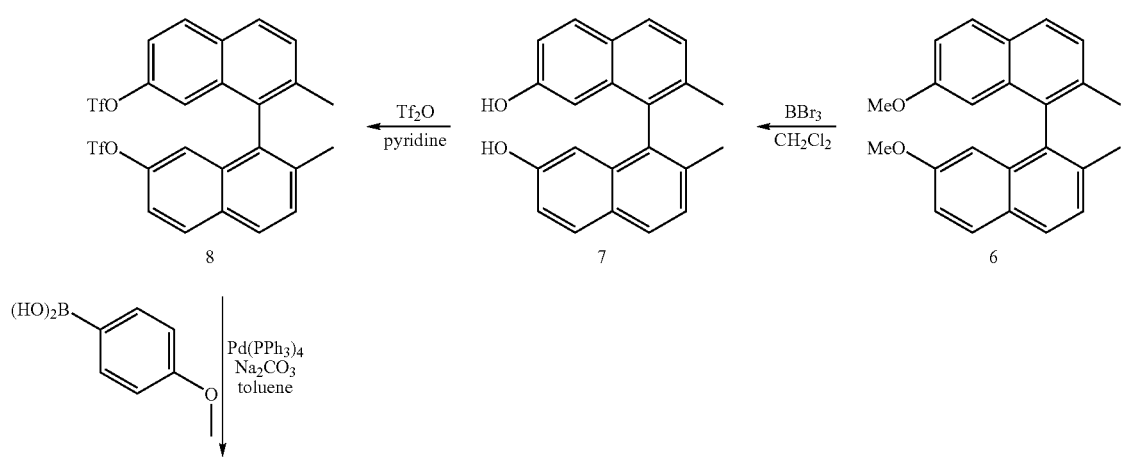
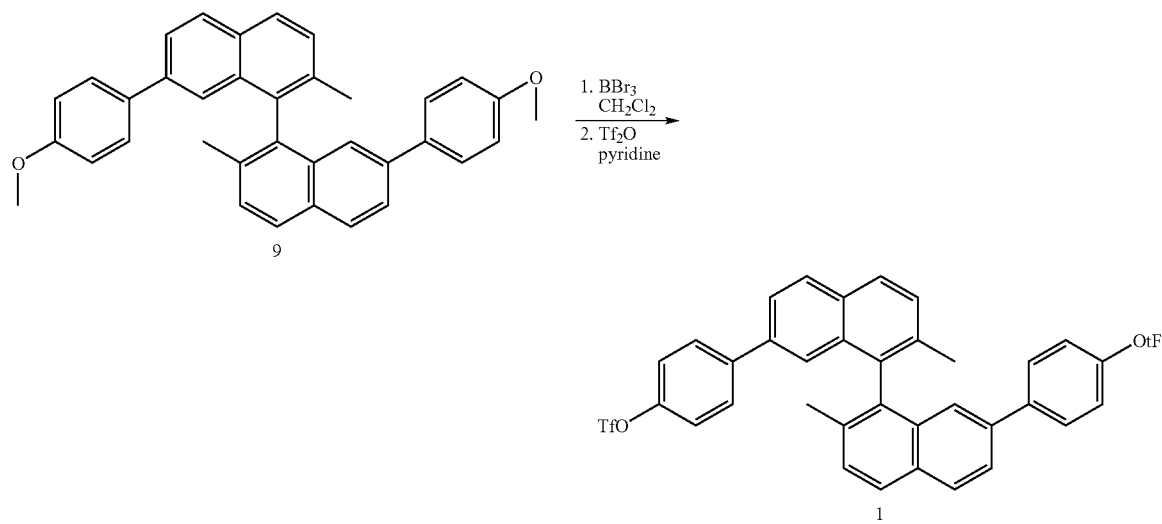

(b) The monomer 3 was synthesized according to the following scheme:

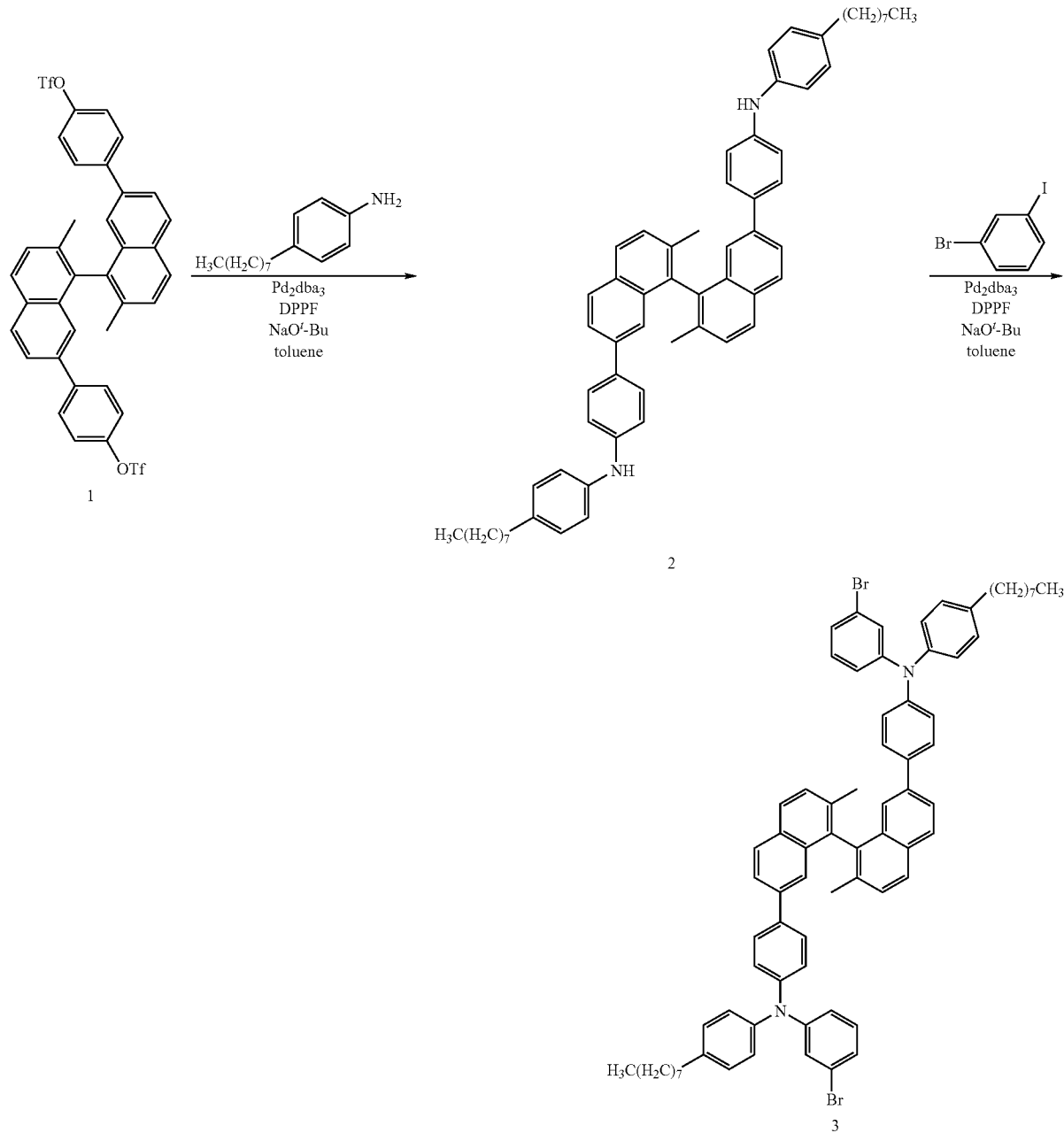

In a nitrogen purged glove box, ditriflate 1 (2 g, 2.73 mmol) and 4-octylaniline (1.18 g, 5.73 mmol, 2.1 eq.) were dissolved in toluene (40 mL) in a 100 mL of round bottom flask, followed by the addition of the toluene (10 mL) solution of tris(dibenzylideneacetone)dipalladium(0) (25 mg, 0.027 eq.) and 1,1'-bis(diphenylphosphino)ferrocene (30 mg, 0.053 eq) to the mixture. After stirring the mixture for 5 min, sodium t-butoxide (0.657 g, 6.82 mmol, 2.5 eq) was added to the resultant solution. The reaction mixture was stirred for 3 days at 90° C. under nitrogen outside glove box. The mixture was passed through a pad of silica gel, which was rinsed with toluene. The combined solution was concentrated on a rotary evaporator, followed by flash column chromatography (30% methylene chloride in hexane) to afford 0.98 g of a white solid as a product. NMR analysis confirmed the structure of intermediate compound 1.

In a nitrogen purged glove box, diamine 2 (0.98 g, 1.16 mmol) and 3-bromo-1-iodobenzene (0.99 g, 3.50 mmol) were dissolved in toluene (30 mL) in a 100 mL of round bottom flask, followed by the addition of the toluene (8 mL) solution of tris(dibenzylideneacetone)dipalladium(0) (29 mg, 0.027 eq.) and 1,1'-bis(diphenylphosphino)ferrocene (34 mg, 0.053 eq) to the mixture. After stirring the mixture for 5 min, sodium t-butoxide (280 mg, 2.91 mmol, 2.5 eq) was added to the resultant solution. The reaction mixture was stirred for 4 days at 90° C. under nitrogen outside glove box.

The mixture was passed through a pad of silica gel, which was rinsed with toluene. The combined solution was concentrated on a rotary evaporator, followed by flash column chromatography (hexane) to afford 1.2 g of a white solid. NMR analysis confirmed the structure of compound 3. (polymer H-1661)

Example 2

The monomer from Example 1 can be polymerized to form Compound C. This can be done using Yamamoto coupling according to the following scheme:

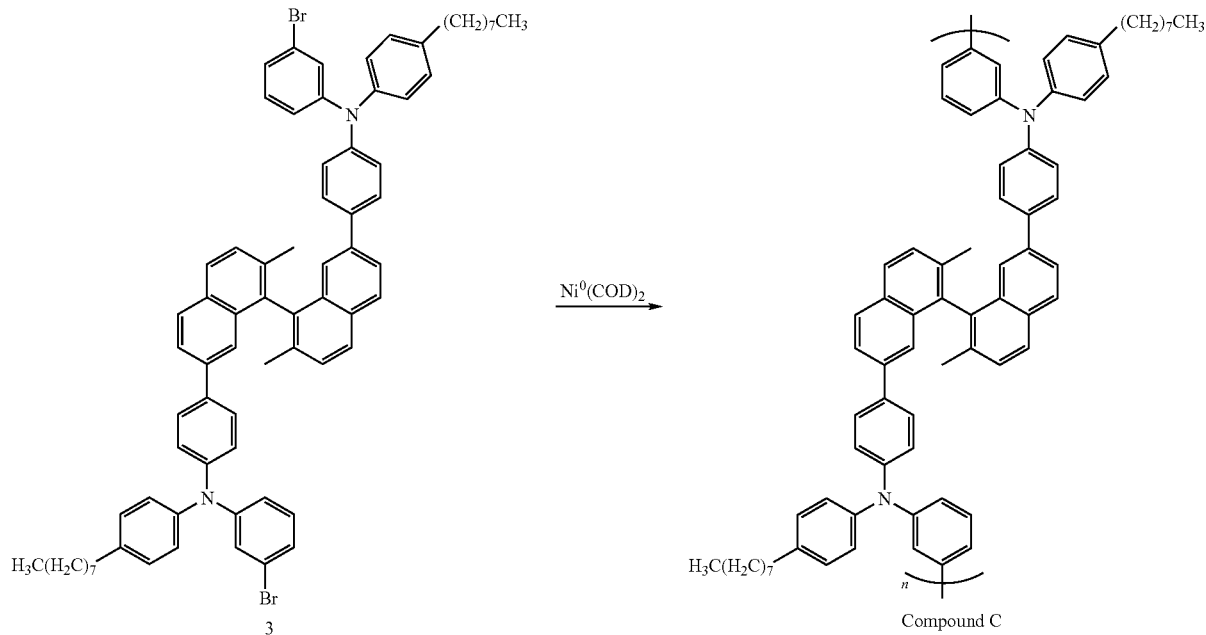

All operations were carried out in a nitrogen purged glovebox unless otherwise noted. Monomer 3 (1.036 g, 0.90 mmol) was added to a scintillation vial and dissolved in 22 mL toluene. A clean, dry 50 mL Schlenk tube was charged with bis(1,5-cyclooctadiene)nickel(0) (0.500 g, 1.818 mmol). 2,2'-Dipyridyl (0.284 g, 1.818 mmol) and 1,5-cyclooctadiene (0.197 g, 1.818 mmol) were weighed into a scintillation vial and dissolved in 5.5 mL N,N'-dimethylformamide. The solution was added to the Schlenk tube. The Schlenk tube was inserted into an aluminum block and the block was heated and stirred on a hotplate/stirrer at a setpoint that resulted in an internal temperature of 60° C. The catalyst system was held at 60° C. for 30 minutes and then raised to 70° C. The monomer solution in toluene was added to the Schlenk tube and the tube was sealed. The polymerization mixture was stirred at 70° C. for 18 h. After 18 h, the Schlenk tube was removed from the block and allowed to cool to room temperature. The tube was removed from the glovebox and the contents were poured into a solution of conc. HCl/MeOH (1.5% v/v conc. HCl). After stirring for 2 h, the polymer was collected by vacuum filtration and dried under high vacuum. The polymer was purified by successive precipitations from toluene into HCl/MeOH (1% v/v conc. HCl), MeOH, toluene (CMOS grade), and 3-pentanone. A white, fibrous polymer (0.200 g) was obtained. The molecular weight of the polymer was determined by GPC (THF mobile phase, polystyrene standards): $M_w=20,486$; $M_n=5,049$; $M_w/M_n=4.06$. NMR analysis confirmed the structure of Compound C.

Example 3

This example illustrates the preparation of a monomer which can be used to form an electroactive compound, Compound D. The monomer 12 was synthesized according to the following scheme:

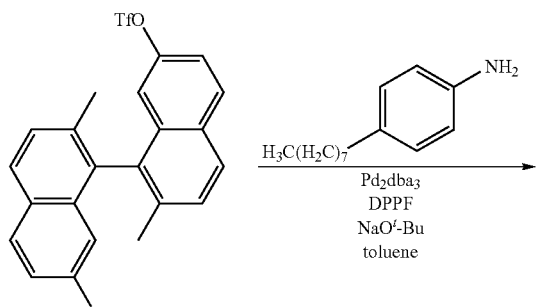

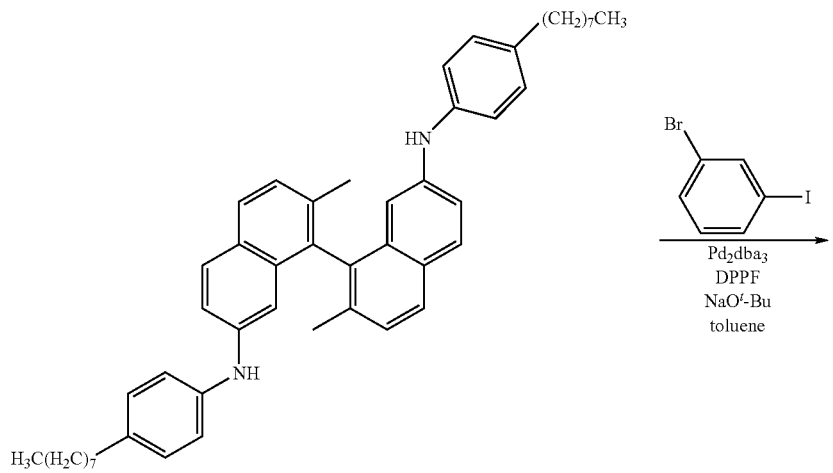

11

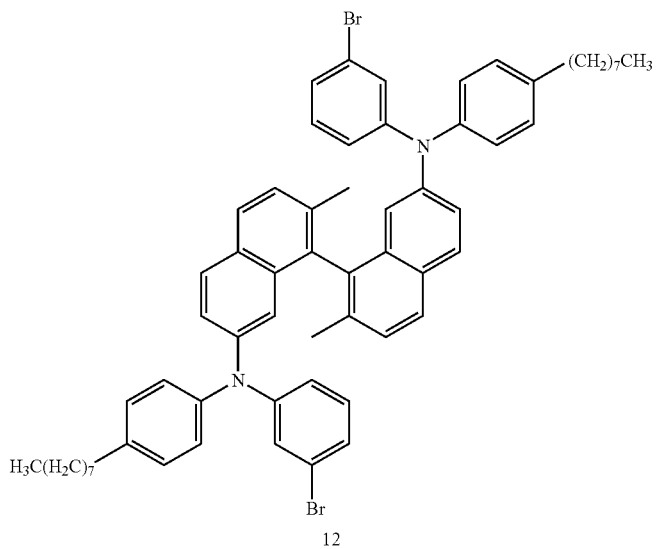

12

In a nitrogen purged glove box, ditriflate 10 (2.72 g, 4.70 mmol) and 4-octylaniline (2.03 g, 9.87 mmol, 2.1 eq.) were dissolved in toluene (30 mL) in a 100 mL of round bottom flask, followed by the addition of the toluene (10 mL) solution of tris(dibenzylideneacetone)dipalladium(0) (43 mg, 0.01 eq.) and 1,1'-bis(diphenylphosphino)ferrocene (52 mg, 0.02 eq) to the mixture. After stirring the mixture for 5 min, sodium t-butoxide (1.13 g, 11.75 mmol, 2.5 eq) was added to the resultant solution. The reaction mixture was stirred overnight at 85° C. under nitrogen outside glove box. The mixture was passed through a pad of silica gel, which was rinsed with toluene. The combined solution was concentrated on a rotary evaporator, followed by flash column chromatography (2% to 10 ethylacetate in hexane, gradient) to afford 2.37 g of a white solid as a product. NMR analysis confirmed the structure of intermediate compound 11.

In a nitrogen purged glove box, diamine 11 (1.45 g, 2.10 mmol) and 3-bromo-1-iodobenzene (1.78 g, 6.3 mmol, 3 eq.) were dissolved in toluene (30 mL) in a 100 mL of round bottom flask, followed by the addition of the toluene (8 mL) solution of tris(dibenzylideneacetone)dipalladium(0) (52 mg, 0.027 eq.) and 1,1'-bis(diphenylphosphino)ferrocene (62 mg, 0.053 eq) to the mixture. After stirring the mixture for 5 min, sodium t-butoxide (504 mg, 5.25 mmol, 2.5 eq) was added to the resultant solution. The reaction mixture was stirred for 3 days at 90° C. under nitrogen outside glove box. The mixture was passed through a pad of silica gel, which was rinsed with toluene. The combined solution was concentrated on a rotary evaporator, followed by flash column chromatography (3% toluene in hexane) to afford 1.5 g of a white solid. NMR analysis confirmed the structure of compound 12.

Example 4

The monomer from Example 3 can be polymerized to form Compound D. This can be done using Yamamoto coupling according to the following scheme:

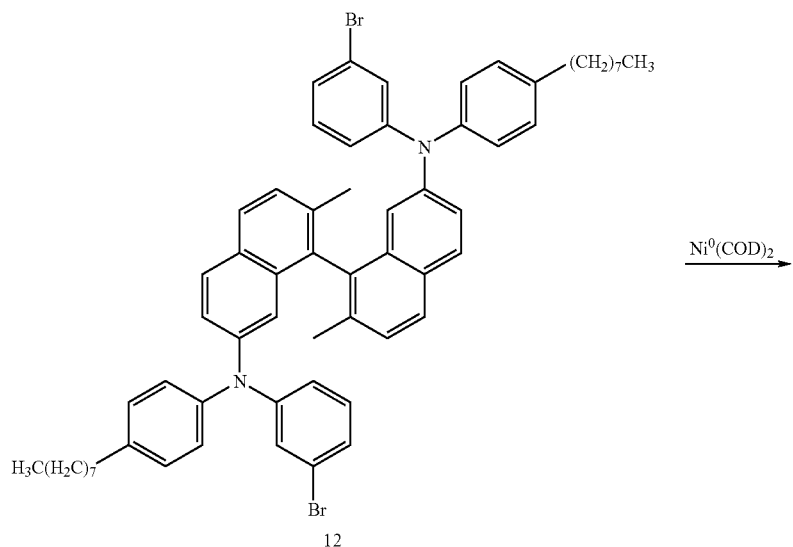

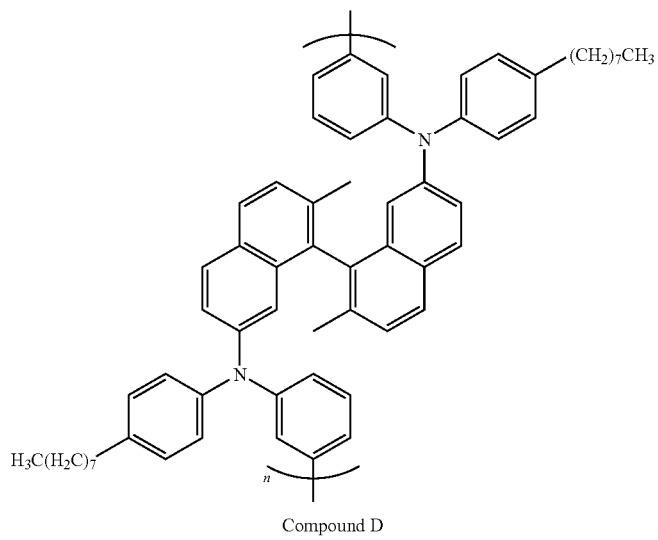

Compound D

The polymerization of compound 12 performed as described for compound C. The polymer was obtained as a white solid in 84.6% yield. The molecular weight of the polymer was determined by GPC (THF mobile phase, polystyrene standards): $M_w=1,846$; $M_n=1,291$; $M_w/M_n=1.43$. NMR analysis confirmed the structure of Compound D.

Example 5

This example illustrates the preparation of a monomer which can be used to form an electroactive compound, Compound A. The monomer 15 was synthesized according to the following scheme:

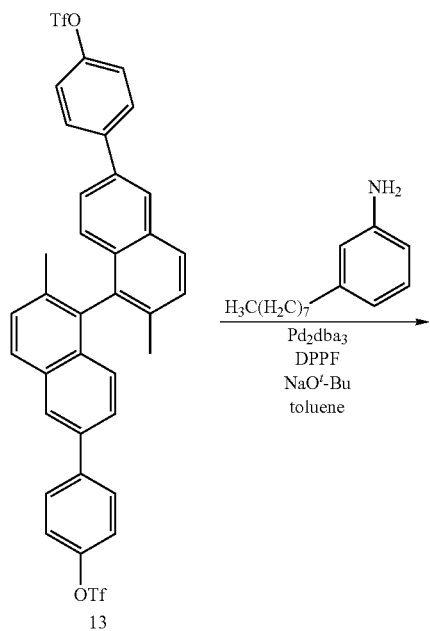

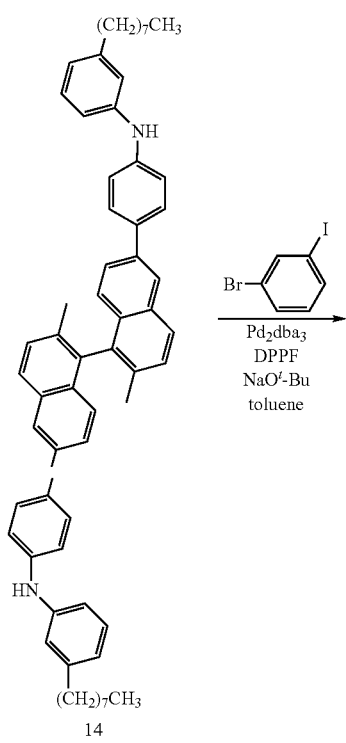

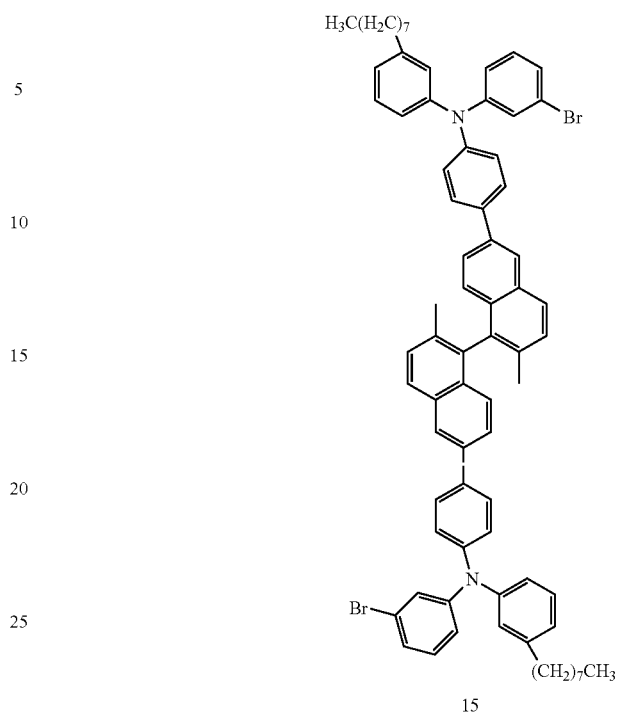

In a nitrogen purged glove box, ditriflate 13 (1.7 g, 2.33 mmol) and 3-octylaniline (1 g, 4.89 mmol) were dissolved in toluene (20 mL) in a 100 mL of round bottom flask, followed by the addition of the toluene (10 mL) solution of tris(dibenzylideneacetone)dipalladium(0) (58 mg, 0.027 eq.) and 1,1'-bis(diphenylphosphino)ferrocene (68 mg, 0.053 eq) to the mixture. After stirring the mixture for 5 min, sodium t-butoxide (0.56 g, 5.82 mmol, 2.5 eq) was added to the resultant solution. The reaction mixture was stirred for 16 h at 85° C. under nitrogen outside glove box. The mixture was passed through a pad of silica gel, which was rinsed with toluene. The combined solution was concentrated on a rotary evaporator, followed by flash column chromatography (10% to 40% methylene chloride in hexane, gradiently) to afford 1.6 g of product. NMR analysis confirmed the structure of intermediate compound 14.

In a nitrogen purged glove box, diamine 14 (1.5 g, 1.78 mmol) and 3-bromo-1-iodobenzene (1.51 g, 5.35 mmol) were dissolved in toluene (40 mL) in a 100 mL of round bottom flask, followed by the addition of the toluene (7 mL) solution of tris(dibenzylideneacetone)dipalladium(0) (47 mg, 0.027 eq.) and 1,1'-bis(diphenylphosphino)ferrocene (53 mg, 0.053 eq) to the mixture. After stirring the mixture for 5 min, sodium t-butoxide (0.428 g, 4.45 mmol, 2.5 eq) was added to the resultant solution. The reaction mixture was stirred for 4 days at 90° C. under nitrogen outside glove box. The mixture was passed through a pad of silica gel, which was rinsed with toluene. The combined solution was concentrated on a rotary evaporator, followed by flash column chromatography (5% toluene in hexane) to afford 1.6 g of a white solid. NMR analysis confirmed the structure of compound 15.

Example 6

The monomer from Example 5 can be polymerized to form Compound A. This can be done using Yamamoto coupling according to the following scheme:

The polymerization of compound 15 was performed as described for compound C. The polymer was obtained as a white solid in 38% yield. The molecular weight of the polymer was determined by GPC (THF mobile phase, polystyrene standards): $M_w$=210,638; $M_n$=33,194; $M_w/M_n$=6.35. NMR analysis confirmed the structure of Compound A.

Example 7

This example illustrates the preparation of a monomer which can be used to form an electroactive compound, Compound B. The monomer 18 was synthesized according to the following scheme:

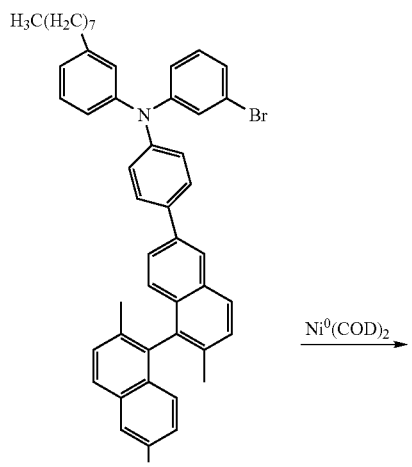

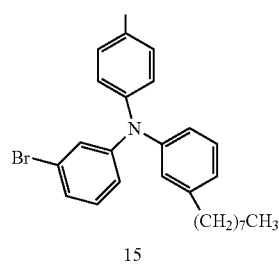

15

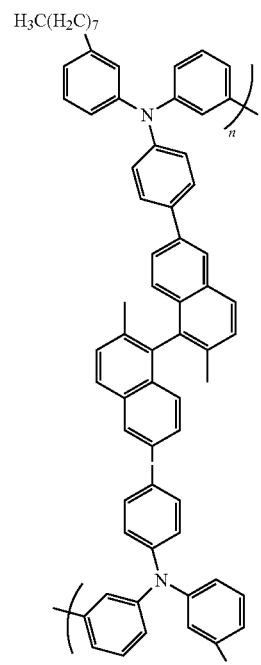

Compound A

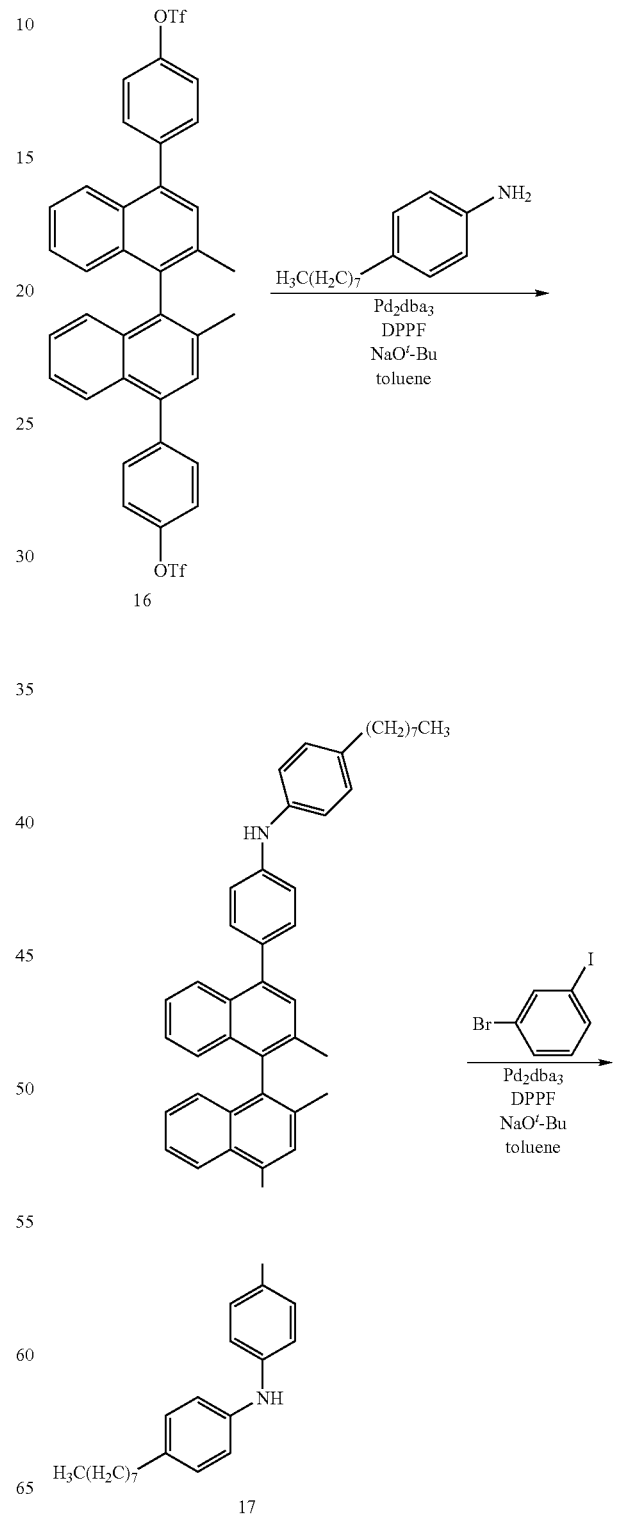

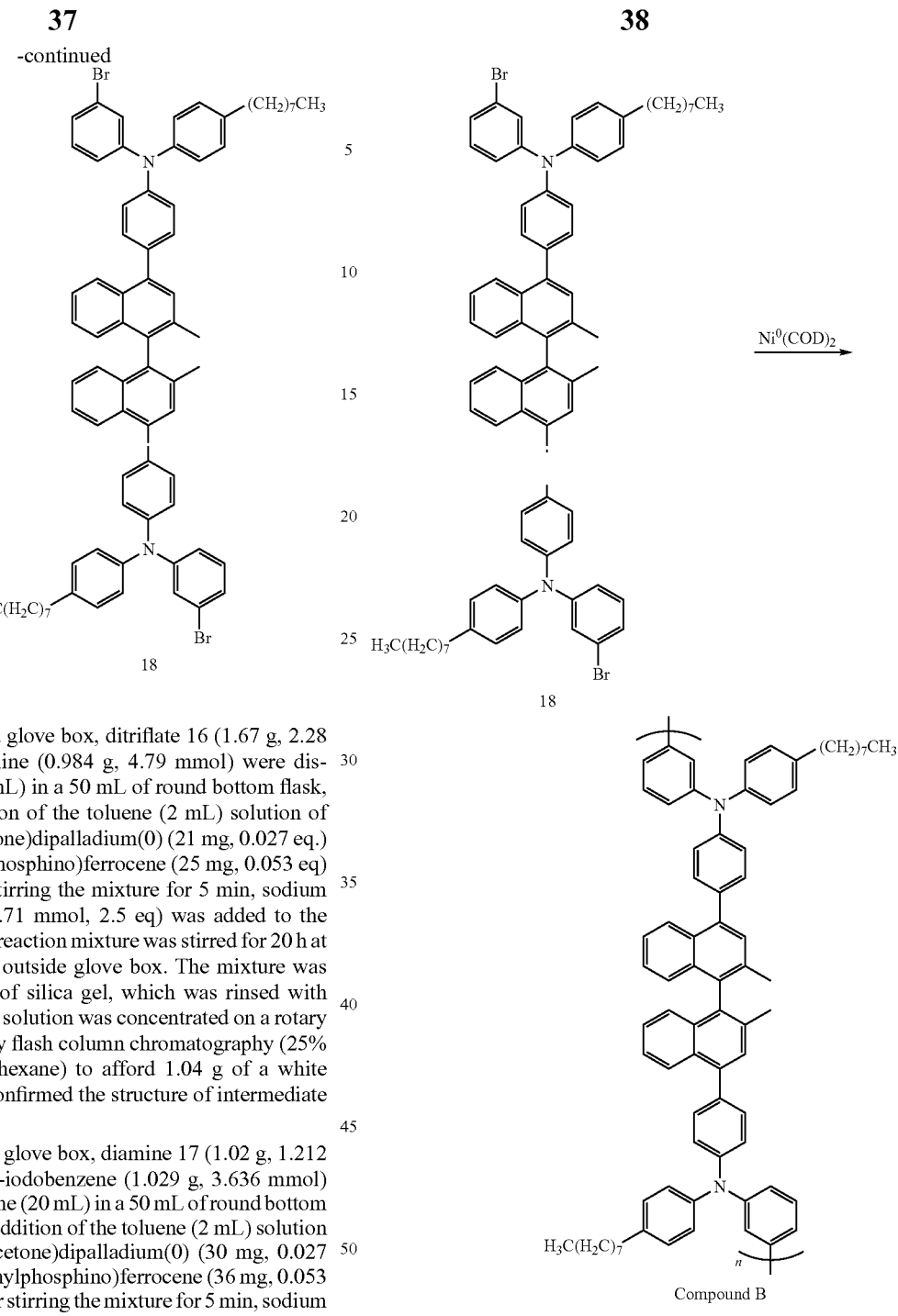

In a nitrogen purged glove box, ditriflate 16 (1.67 g, 2.28 mmol) and 4-octylaniline (0.984 g, 4.79 mmol) were dissolved in toluene (20 mL) in a 50 mL of round bottom flask, followed by the addition of the toluene (2 mL) solution of tris(dibenzylideneacetone)dipalladium(0) (21 mg, 0.027 eq.) and 1,1'-bis(diphenylphosphino)ferrocene (25 mg, 0.053 eq) to the mixture. After stirring the mixture for 5 min, sodium t-butoxide (0.548 g, 5.71 mmol, 2.5 eq) was added to the resultant solution. The reaction mixture was stirred for 20 h at 85° C. under nitrogen outside glove box. The mixture was passed through a pad of silica gel, which was rinsed with toluene. The combined solution was concentrated on a rotary evaporator, followed by flash column chromatography (25% methylenechloride in hexane) to afford 1.04 g of a white solid. NMR analysis confirmed the structure of intermediate compound 17.

In a nitrogen purged glove box, diamine 17 (1.02 g, 1.212 mmol) and 3-bromo-1-iodobenzene (1.029 g, 3.636 mmol) were dissolved in toluene (20 mL) in a 50 mL of round bottom flask, followed by the addition of the toluene (2 mL) solution of tris(dibenzylideneacetone)dipalladium(0) (30 mg, 0.027 eq.) and 1,1'-bis(diphenylphosphino)ferrocene (36 mg, 0.053 eq) to the mixture. After stirring the mixture for 5 min, sodium t-butoxide (291 mg, 3.03 mmol, 2.5 eq) was added to the resultant solution. The reaction mixture was stirred for 24 h at 85° C. under nitrogen outside glove box. The mixture was passed through a pad of silica gel, which was rinsed with toluene. The combined solution was concentrated on a rotary evaporator, followed by flash column chromatography (10% toluene in hexane) to afford 1.2 g of a white solid. NMR analysis confirmed the structure of compound 18.

Example 8

The monomer from Example 7 can be polymerized to form Compound B. This can be done using Yamamoto coupling according to the following scheme:

The polymerization of compound 18 was performed as described for compound B. The polymer was obtained as a white solid in 50% yield. The molecular weight of the polymer was determined by GPC (THF mobile phase, polystyrene standards): $M_w$=213,649; $M_n$=102,594; $M_w/M_n$=2.08. NMR analysis confirmed the structure of compound B.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A polymer having a formula selected from the group consisting of Formula Ia, Formula Ic, and Formula Ie:

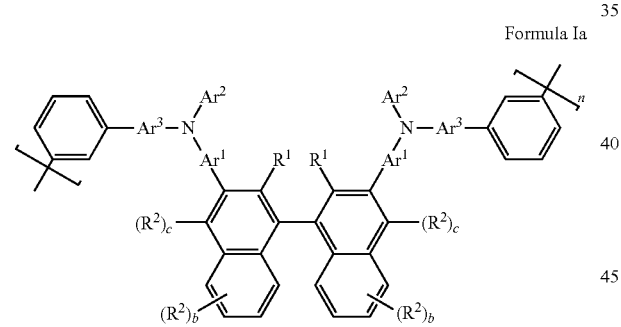

Formula Ia

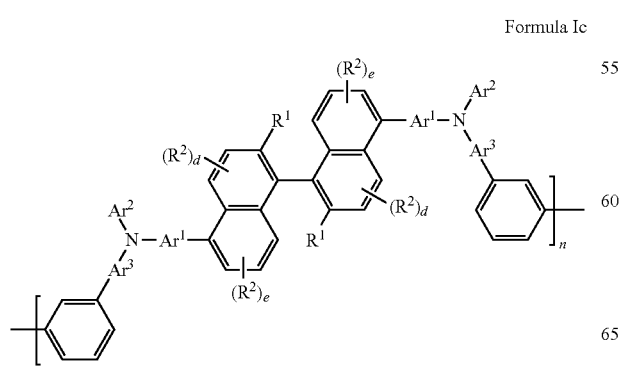

Formula Ic

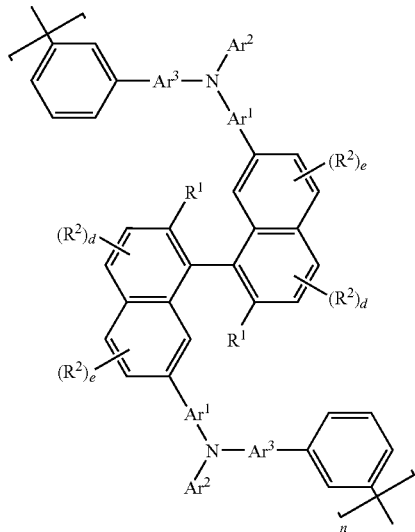

Formula Ie wherein:
$Ar^1$ is a single bond;
$Ar^2$ is the same or different at each occurrence and is an aryl group;
$Ar^3$ is the same or different at each occurrence and is an arylene;
$R^1$ is the same or different at each occurrence and is selected from the group consisting of H, D, aryl groups, alkyl groups, silyl groups, siloxane groups, fluoroalkyl groups, alkoxy groups, and fluoroalkoxy groups, or the two $R^1$ groups may be joined together to form an aliphatic ring having 5-10 carbons;
$R^2$ is the same or different at each occurrence and is selected from the group consisting of D, aryl groups, alkyl groups, silyl groups, siloxane groups, fluoroalkyl groups, alkoxy groups, and fluoroalkoxy groups;
n is an integer equal to or greater than 20;
b is the same or different at each occurrence and is an integer from 0 to 4;
c is the same or different at each occurrence and is an integer from 0 to 1;
d is the same or different at each occurrence and is an integer from 0 to 2; and
e is the same or different at each occurrence and is an integer from 0 to 3.

2. The compound of claim 1, wherein $Ar^2$ is selected from the group consisting of naphthyl and a group having Formula IV

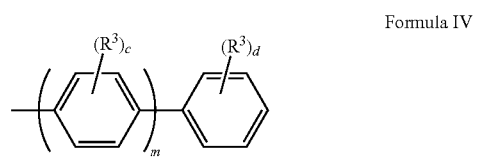

Formula IV where:
$R^3$ is the same or different at each occurrence and is selected from the group consisting of alkyl, alkoxy, siloxane and silyl;
c is the same or different at each occurrence and is an integer from 0-4;

d is an integer from 0-5; and
m is an integer from 1 to 6.

3. The compound of claim 1, wherein $Ar^3$ is selected from the group consisting of naphthylene, and a group having Formula III

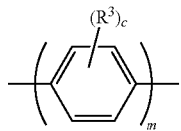

Formula III $R^3$ is the same or different at each occurrence and is selected from the group consisting of alkyl, alkoxy, siloxane and silyl;
c is the same or different at each occurrence and is an integer from 0-4; and
m is an integer from 1 to 6.

4. A polymer having a formula selected from the group consisting of Formula Ia, Formula Ic, and Formula Ie:

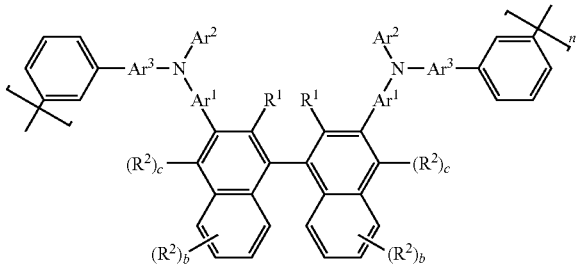

Formula Ia

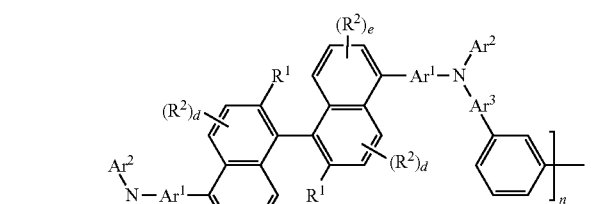

Formula Ic

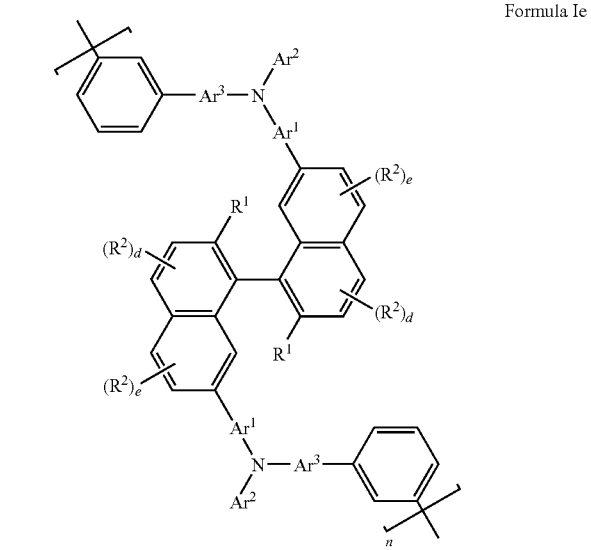

Formula Ie wherein:
$Ar^1$ is a single bond;
$Ar^2$ is the same or different at each occurrence and is an aryl group;
$Ar^3$ is the same or different at each occurrence and is selected from the group consisting of a single bond and an arylene;
$R^1$ is the same or different at each occurrence and is selected from the group consisting of H, D, aryl groups, alkyl groups, silyl groups, siloxane groups, fluoroalkyl groups, alkoxy groups, and fluoroalkoxy groups, or the two $R^1$ groups may be joined together to form an aliphatic ring having 5-10 carbons;
$R^2$ is the same or different at each occurrence and is selected from the group consisting of D, aryl groups, alkyl groups, silyl groups, siloxane groups, fluoroalkyl groups, alkoxy groups, and fluoroalkoxy groups;
n is an integer equal to or greater than 20;
b is the same or different at each occurrence and is an integer from 0 to 4;
c is the same or different at each occurrence and is an integer from 0 to 1;
d is the same or different at each occurrence and is an integer from 0 to 2; and
e is the same or different at each occurrence and is an integer from 0 to 3,
wherein crosslinking substituents are present on at least one $Ar^2$.

5. The compound of claim 1, wherein $R^1$ is selected from an alkyl group having 1-12 carbon atoms and an alkoxy group having 1-12 carbon atoms.

6. The compound of claim 1, wherein $R^2$ is selected from an alkyl group having 1-12 carbon atoms and an alkoxy group having 1-12 carbon atoms.

7. An organic electronic device comprising a first electrical contact layer, a second electrical contact layer and an active layer therebetween, wherein the active layer comprises a compound having a formula selected from the group consisting of Formula Ia, Formula Ic, and Formula Ie:

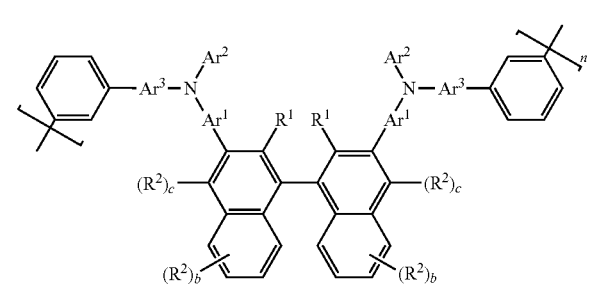

Formula Ia

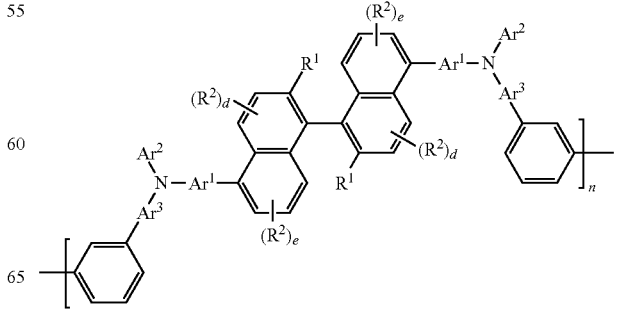

Formula Ic

-continued

Formula Ie

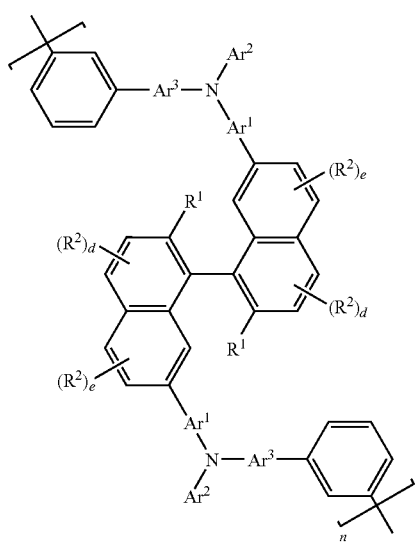

wherein:
$Ar^1$ is a single bond;
$Ar^2$ is the same or different at each occurrence and is an aryl group;
$Ar^3$ is the same or different at each occurrence and is an arylene;
$R^1$ is the same or different at each occurrence and is selected from the group consisting of H, D, aryl groups, alkyl groups, silyl groups, siloxane groups, fluoroalkyl groups, alkoxy groups, and fluoroalkoxy groups, or the two $R^1$ groups may be joined together to form an aliphatic ring having 5-10 carbons;
$R^2$ is the same or different at each occurrence and is selected from the group consisting of D, aryl groups, alkyl groups, silyl groups, siloxane groups, fluoroalkyl groups, alkoxy groups, and fluoroalkoxy groups;
n is an integer equal to or greater than 20;
b is the same or different at each occurrence and is an integer from 0 to 4;
c is the same or different at each occurrence and is an integer from 0 to 1;
d is the same or different at each occurrence and is an integer from 0 to 2; and
e is the same or different at each occurrence and is an integer from 0 to 3.

8. The device of claim 7, wherein $Ar^1$ has Formula III

Formula III

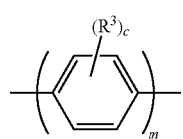

where:
$R^3$ is the same or different at each occurrence and is selected from the group consisting of alkyl, alkoxy, siloxane and silyl;
c is the same or different at each occurrence and is an integer from 0-4; and
m is an integer from 1 to 6.

9. The device of claim 7, wherein $Ar^2$ is selected from the group consisting of naphthyl and a group having Formula IV Formula IV

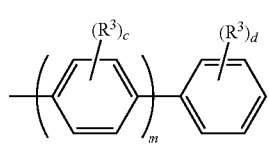

where:
$R^3$ is the same or different at each occurrence and is selected from the group consisting of alkyl, alkoxy, siloxane and silyl;
c is the same or different at each occurrence and is an integer from 0-4;
d is an integer from 0-5; and
m is an integer from 1 to 6.

10. The device of claim 7, wherein $Ar^3$ is selected from the group consisting of naphthylene, and a group having Formula III Formula III

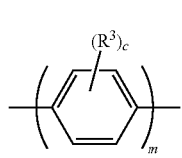

where:
$R^3$ is the same or different at each occurrence and is selected from the group consisting of alkyl, alkoxy, siloxane and silyl;
c is the same or different at each occurrence and is an integer from 0-4; and
m is an integer from 1 to 6.

11. An organic electronic device comprising a first electrical contact layer, a second electrical contact layer and an active layer therebetween, wherein the active layer comprises a compound having a formula selected from the group consisting of Formula Ia, Formula Ic, and Formula Ie:

Formula Ia

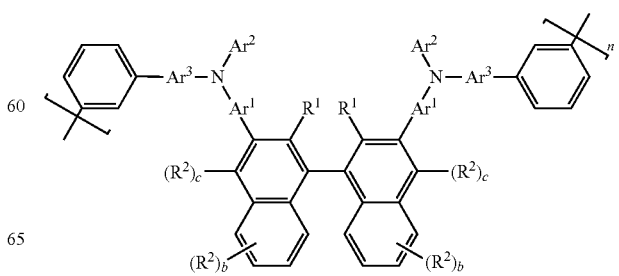

-continued

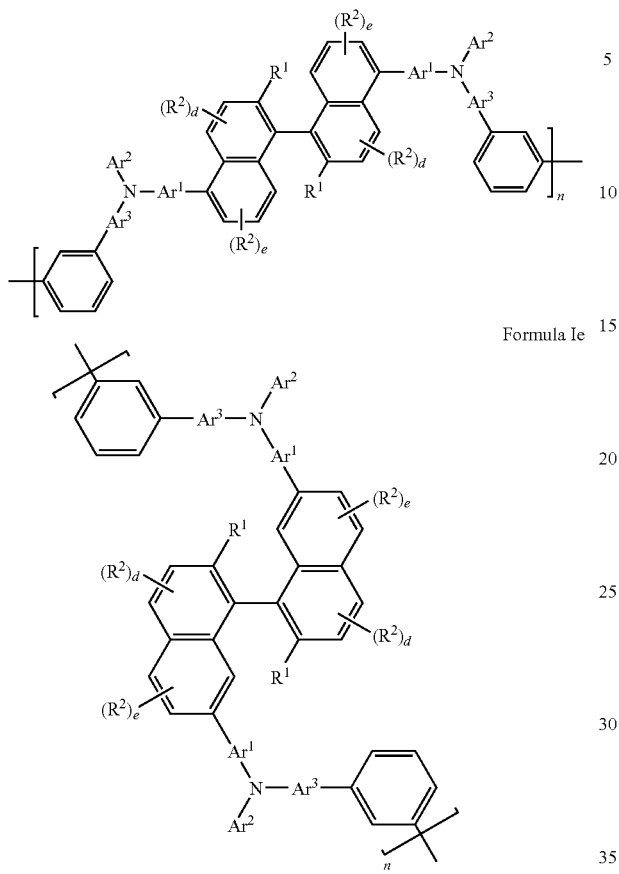

Formula Ic

Formula Ie wherein:
Ar¹ is a single bond;
Ar² is the same or different at each occurrence and is an aryl group;
Ar³ is the same or different at each occurrence and is selected from the group consisting of a single bond and an arylene;
R¹ is the same or different at each occurrence and is selected from the group consisting of H, D, aryl groups, alkyl groups, silyl groups, siloxane groups, fluoroalkyl groups, alkoxy groups, and fluoroalkoxy groups, or the two R¹ groups may be joined together to form an aliphatic ring having 5-10 carbons;
R² is the same or different at each occurrence and is selected from the group consisting of D, aryl groups, alkyl groups, silyl groups, siloxane groups, fluoroalkyl groups, alkoxy groups, and fluoroalkoxy groups;
n is an integer equal to or greater than 20;
b is the same or different at each occurrence and is an integer from 0 to 4;
c is the same or different at each occurrence and is an integer from 0 to 1;
d is the same or different at each occurrence and is an integer from 0 to 2; and
e is the same or different at each occurrence and is an integer from 0 to 3,
wherein a crosslinking substituent is present on at least one Ar².

12. The device of claim 7, wherein the active layer is a hole transport layer and the layer consists essentially of a compound having a formula selected from the group consisting of Formula Ia, Formula Ic, and Formula Ie.

13. The device of claim 7, wherein the active layer is a photoactive layer.

14. The polymer of claim 4, wherein Ar² is selected from the group consisting of naphthyl and a group having Formula IV

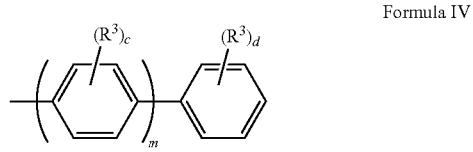

Formula IV where:
R³ is the same or different at each occurrence and is selected from the group consisting of alkyl, alkoxy, siloxane and silyl;
c is the same or different at each occurrence and is an integer from 0-4;
d is an integer from 0-5; and
m is an integer from 1 to 6.

15. The polymer of claim 4, wherein Ar³ is selected from the group consisting of a single bond, naphthylene, and a group having Formula III

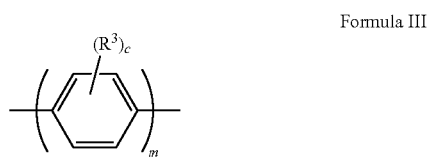

Formula III where:
R³ is the same or different at each occurrence and is selected from the group consisting of alkyl, alkoxy, siloxane and silyl;
c is the same or different at each occurrence and is an integer from 0-4; and
m is an integer from 1 to 6.

16. The polymer of claim 4, wherein R¹ is selected from an alkyl group having 1-12 carbon atoms and an alkoxy group having 1-12 carbon atoms.

17. The polymer of claim 4, wherein R² is selected from an alkyl group having 1-12 carbon atoms and an alkoxy group having 1-12 carbon atoms.

18. The device of claim 11, wherein Ar¹ has Formula III

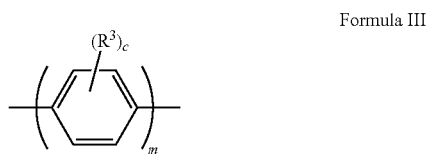

Formula III where:
R³ is the same or different at each occurrence and is selected from the group consisting of alkyl, alkoxy, siloxane and silyl;
c is the same or different at each occurrence and is an integer from 0-4; and
m is an integer from 1 to 6.

19. The device of claim 11, wherein $Ar^2$ is selected from the group consisting of naphthyl and a group having Formula IV

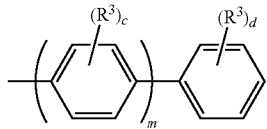

Formula IV where:
- $R^3$ is the same or different at each occurrence and is selected from the group consisting of alkyl, alkoxy, siloxane and silyl;
- c is the same or different at each occurrence and is an integer from 0-4;
- d is an integer from 0-5; and
- m is an integer from 1 to 6.

20. The device of claim 11, wherein $Ar^3$ is selected from the group consisting of a single bond, naphthylene, and a group having Formula III

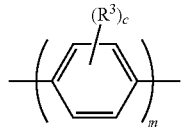

Formula III where:
- $R^3$ is the same or different at each occurrence and is selected from the group consisting of alkyl, alkoxy, siloxane and silyl;
- c is the same or different at each occurrence and is an integer from 0-4; and
- m is an integer from 1 to 6.

21. The device of claim 11, wherein the active layer is a hole transport layer and the layer consists essentially of a compound having a formula selected from the group consisting of Formula Ia, Formula Ic, and Formula Ie.

22. The device of claim 11, wherein the active layer is a photoactive layer.

* * * * *